(12) United States Patent
De Lombaert et al.

(10) Patent No.: US 8,193,214 B2
(45) Date of Patent: Jun. 5, 2012

(54) CHYMASE INHIBITORS

(75) Inventors: Stéphane De Lombaert, Madison, CT (US); Michel Jose Emmanuel, New Fairfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 433 days.

(21) Appl. No.: 12/443,498

(22) PCT Filed: Sep. 27, 2007

(86) PCT No.: PCT/US2007/079660
§ 371 (c)(1),
(2), (4) Date: Mar. 30, 2009

(87) PCT Pub. No.: WO2008/045688
PCT Pub. Date: Apr. 17, 2008

(65) Prior Publication Data
US 2010/0029637 A1     Feb. 4, 2010

Related U.S. Application Data

(60) Provisional application No. 60/828,441, filed on Oct. 6, 2006.

(51) Int. Cl.
*A01N 43/42* (2006.01)
*A01N 43/52* (2006.01)
*A61K 31/44* (2006.01)
*A61K 31/415* (2006.01)
*C07D 413/00* (2006.01)
*C07D 491/02* (2006.01)
*C07D 498/02* (2006.01)

(52) U.S. Cl. ......... 514/300; 514/393; 544/127; 546/121
(58) Field of Classification Search ................. 514/300, 514/393; 544/127; 546/121
See application file for complete search history.

(56) References Cited

FOREIGN PATENT DOCUMENTS

| JP | 06/131559 A | 5/2006 |
|---|---|---|
| WO | 01/53298 A1 | 7/2001 |
| WO | 2005/073214 A2 | 8/2005 |
| WO | 2006/096444 A2 | 9/2006 |
| WO | WO 2006114261 A1 * | 11/2006 |

OTHER PUBLICATIONS

International Search Report for PCT/US2007/079660 dated Feb. 22, 2008.

* cited by examiner

*Primary Examiner* — Sreeni Padmanabhan
*Assistant Examiner* — Kendra D Carter
(74) *Attorney, Agent, or Firm* — Michael P. Morris; Anthony P. Bottino; Usha R. Patel

(57) ABSTRACT

Disclosed are small molecule inhibitors which are useful in treating various diseases and conditions involving chymase.

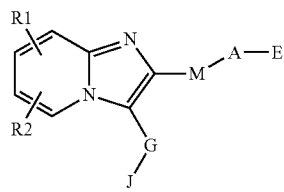

8 Claims, No Drawings

CHYMASE INHIBITORS

APPLICATION DATA

This application is a 371 National Stage filing of PCT/US2007/079660 filed on Sep. 27, 2007. This application also claims benefit to U.S. provisional application Ser. No. 60/828,441 filed on Oct. 6, 2006.

FIELD OF THE INVENTION

The invention relates to small molecule inhibitors which are useful in treating various diseases and conditions involving Chymase.

BACKGROUND OF THE INVENTION

In cardiac tissue of cardiomyopathic patients, transforming growth factor-β (TGF-β), which has been demonstrated to stimulate cardiac fibrosis in animal models (Kuwahara, et al. Circulation, 2002, 106, 130), is increased (Li et al., Circulation, 1997, 96, 874). In the myocardial fibrotic area, it is known that mast cells are increased in number and may contribute to the development of fibroblast proliferation in cardiac tissues of patients with cardiomyopathy (Patella et al., Circulation, 1998, 97, 971). Chymase is a chymotrypsin-like serine protease contained in the secretory granules of mast cells. Although the precise physiological roles of Chymase have not been completely revealed, Chymase is known to transform angiotensin I to angiotensin II and may contribute to activation of TGF-β, matrix proteases, and cytokines (Taipale et al., J. Biol. Chem., 1995, 270, 4689; Takai et al., Life Sci., 1996, 58, 591; Takai et al., Circulation, 1999, 100, 654).

A potent and selective Chymase inhibitor may have potential use as a treatment of chronic heart failure, atherosclerosis, restenosis, and myocardial infarction by inhibiting local production of angiotensin II in the heart and release of TGF-β, two independent mediators of cardiac remodeling. An inhibitor may also have potential use for treatment of mast cell mediated diseases such as dermatitis, asthma, chronic obstructive pulmonary disease (COPD), and pulmonary inflammation, since Chymase is implicated in microvascular leakage, neutrophil accumulation, the stimulation of mucus secretion, and the modulation of cytokines (He et al., Eur. J. Pharmacol., 1998, 352, 91).

Several small molecule Chymase inhibitors have been reported to be efficacious in the cardiomyopathic hamster model of heart failure (Takai et al. J. Pharmacol. Exp. Ther. 2003, 305, 17), in carotid artery injury by a balloon catheter in dogs (Takai et al. J. Pharmacol. Exp. Ther, 2003, 304, 841), and in the hamster left anterior descending coronary artery ligation model of heart failure (WO 03/018061). Additionally, a Chymase inhibitor has been demonstrated to be efficacious in a sheep asthma model (WO 2005/073214). However, there is no example of commercialization of a Chymase inhibitor as a medicament.

SUMMARY OF THE INVENTION

It is therefore an object of the invention to provide a small molecule a Chymase inhibitor as defined herein, and pharmaceutical compositions thereof.

It is also an object of the invention to provide methods of using said Chymase inhibitors to treat various diseases and conditions related thereto.

It is a further object of the invention to provide processes of preparing said Chymase inhibitors.

DETAILED DESCRIPTION OF THE INVENTION

In one generic aspect of the invention, there is provided a compound of the formula (I):

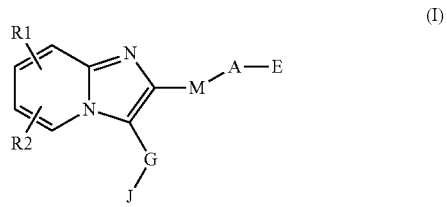

R1 and R2 are independently hydrogen, halogen, trihaloalkyl, trihaloalkoxy, cyano, hydroxyl, $C_{1-4}$ alkyl, $C_{1-4}$ alkoxy, —CORd, —COORd, —CON(Rc)Rd, —N(Rc)Rd, —N(Rc)CORd wherein each Rd is independently a hydrogen, $C_{1-6}$ linear or branched alkyl or cycloalkyl, $C_{1-6}$ linear or branched alkenyl or heterocyclyl or where R1 and R2 together represent —O—$CH_2$—O—, —O—$CH_2$—$CH_2$—O— or —$CH_2$—$CH_2$—$CH_2$—, wherein each group is optionally independently substituted with one to three substituents chosen from $C_{1-4}$ acyl, $C_{1-4}$ alkyl, $C_{1-4}$ alkoxy, amino, dialkylamino, cyano, carboxy, carboxamido, halogen, hydroxyl and phenyl optionally substituted with halogens;

A is $C_1$-$C_7$ linear, branched or cyclic alkyl group optionally interrupted by one or more —O—, —S—, —SO—, —$SO_2$— and —NRa— optionally substituted with one to three substituents chosen from halogen, $C_{1-6}$ linear or branched alkyl, $C_{1-6}$ linear or branched alkoxy, $C_{1-6}$ linear or branched alkylthio, $C_{1-6}$ linear or branched alkylsulfonyl, phenyl and oxo;

E is —COORe, —$SO_3$Re, —CONHRe, —$SO_2$NHRe, —$NHSO_2$Re, —$CONHSO_2$Re, —$SO_2$NH—CO(Rf), heteroaryl, heterocycyl, wherein each Re is independently hydrogen, $C_{1-4}$ alkyl or aryl, and Rf is $C_{1-4}$ alkyl or aryl;

G is $C_{1-6}$ linear or branched alkyl optionally interrupted by one or more of —O—, —S—, —$SO_2$ or —NRa—, wherein the alkyl group is optionally substituted with hydroxyl, cyano, $C_{1-6}$ linear or branched alkyl or $C_{1-6}$ linear or branched alkoxy;

M is a methylene group, oxygen, —N(Rb)-, or —$S(O)_m$—, where m is an integer of 0-2; and, wherein the said methylene group is optionally substituted by one to two substituents chosen from hydroxyl, cyano, $C_{1-6}$ linear or branched alkyl, $C_{1-6}$ linear or branched alkoxy, trihalomethyl, trihalomethoxy, phenyl and oxo;

J is an optionally mono- or poly-substituted aromatic carbocycle or a heteroaromatic group having 4-10 carbon atoms containing one or more hetero atoms chosen from the group consisting of an oxygen atom, a nitrogen atom and a sulfur atom in its ring(s); each substituent on said aromatic or heteroaromatic groups is chosen from halogen, hydroxyl, cyano, $C_{1-6}$ linear or branched alkyl, $C_{1-6}$ linear or branched alkoxy, $C_{1-6}$ linear or branched alkylthio, $C_{1-6}$ linear or branched alkylsulfonyl, phenylsulfonyl, $C_{1-6}$ linear or branched acyl, $C_{1-6}$ linear or branched acylamino, trihalomethyl, trihalomethoxy, phenyl, oxo, —COORa, —CON(Rc)Ra, $SO_2N(Rc)$Ra, —N(Rc)Ra and phenoxy optionally substituted by one or more halogens;

Ra, Rb and Rc are each independently C1-3 alkyl or hydrogen;

or the pharmaceutically acceptable salts thereof.

In another embodiment there is provided a compound according to the embodiment immediately above and wherein:

R1 and R2 are attached as follows:

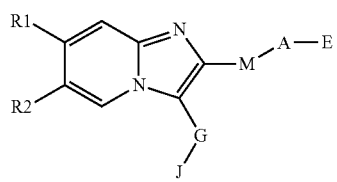

and are independently hydrogen, Cl, Br, F, I, trihaloalkyl, trihaloalkoxy cyano, hydroxyl, $C_{1-4}$ alkyl, $C_{1-4}$ alkoxy, —CORd, —COORd, —CON(Rc)Rd, —N(Rc)Rd, —N(Rc)CORd wherein each Rd is independently a hydrogen, $C_{1-6}$ linear or branched alkyl or cycloalkyl, $C_{1-6}$ linear or branched alkenyl or heterocyclyl chosen from pyrrole, pyrrolidinyl, pyrazole, imidazole, furan, tetrahydrofuran, oxazole, thiophene, tetrahydrothiophene and thiazole wherein for each ring possessing a sulfur heteroatom the sulfur is —S—, —S(O)— or —S(O)$_2$—, or where R1 and R2 together represent —O—CH$_2$—O—, —O—CH$_2$—CH$_2$—O— or —CH$_2$—CH$_2$—CH$_2$—, wherein each group is optionally independently substituted with one to three substituents chosen from $C_{1-4}$ acyl, $C_{1-4}$ alkyl, $C_{1-4}$ alkoxy, amino, dialkylamino, cyano, carboxy, carboxamido, Cl, Br, F, I, hydroxyl and phenyl optionally substituted with one to three Cl, Br, F, I;

A is $C_1$-$C_7$ linear, branched optionally independently substituted with one to three substituents chosen from amino, cyano, carboxy, carboxamido, halogen, hydroxyl, nitro, phenyl, $C_{1-6}$ linear or branched alkyl and $C_{1-6}$ linear or branched alkoxy;

E is —COORe, —SO$_3$Re, —CONHRe, —CONHSO$_2$Re, —SO$_2$NH—CO(Rf), tetrazol-5-yl, 5-oxo-1,2,4-oxadiazol-3-yl, 5-oxo-1,2,4-thiadiazol-3-yl, 5-thioxo-1,2,4-oxadiazol-3-yl, 5-thioxo-1,2,4-thiadiazol-3-yl, 3-oxo-1,2,4-oxadiazol-5-yl, N3,5-dioxo-5-oxadiazolidino, 2-oxo1,3,4-oxadiazol-2-yl, 3-oxo1,2,4-triazol-5-yl or 2,dioxo-benzothiadiazin-6-yl, wherein each Re is independently hydrogen, $C_{1-4}$ alkyl or phenyl, and Rf is $C_{1-4}$ alkyl or aryl;

G is $C_{1-4}$ linear or branched alkyl optionally substituted with a substituent chosen from hydroxyl, a cyano, $C_{1-6}$ linear or branched alkyl and $C_{1-6}$ linear or branched alkoxy;

M is a methylene group, oxygen, —N(Rb)-, or —S(O)$_m$—, where m is an integer of 0-2;

J is an optionally mono- or di-substituted phenyl, naphthyl, benzothienyl, benzopyrrolyl, benzimidazolyl, indolyl; each substituent on said aromatic or heteroaromatic groups is chosen from halogen, hydroxyl, cyano, $C_{1-4}$ linear or branched alkyl, $C_{1-4}$ linear or branched alkoxy, $C_{1-6}$ linear or branched alkylthio, $C_{1-6}$ linear or branched alkylsulfonyl, phenylsulfonyl, $C_{1-6}$ linear or branched acyl, $C_{1-6}$ linear or branched acylamino, trihalomethyl, trihalomethoxy, phenyl, oxo, —COORa, —CON(Rc)Ra, —SO$_2$N(Rc)Ra, N(Rc)Ra and phenoxy optionally substituted by one or more halogens.

In another embodiment there is provided a compound according to the embodiment immediately above and wherein:

R1 and R2 are independently hydrogen, Cl, F, trihalomethyl, trihalomethoxy, cyano, hydroxyl, $C_{1-2}$ alkyl, $C_{1-4}$ alkoxy, —CORd, —CON(Rc)Rd, —N(Rc)Rd, —N(Rc)CORd wherein each Rd is independently a hydrogen or $C_{1-6}$ linear or branched alkyl, $C_{1-6}$ linear or branched alkenyl, furan, tetrahydrofuran, thiophene and tetrahydrothiophene wherein for each ring possessing a sulfur heteroatom the sulfur is —S—, —S(O)— or —S(O)$_2$— or where R1 and R2 together represent —O—CH$_2$—CH$_2$—O—, wherein each group is optionally independently substituted with one to three substituents chosen from $C_{1-4}$ alkyl, $C_{1-4}$ alkoxy amino, cyano, carboxy, carboxamido, Cl, Br, F, I, and hydroxyl;

A is a —(CH$_2$)$_3$— group, optionally substituted with one substituent chosen from phenyl and $C_{1-3}$ alkyl;

E is —COORe wherein Re is hydrogen or methyl;

G is $C_{1-2}$ alkyl;

M is a methylene group, oxygen, —NH—, —N(CH$_3$)— or sulfur;

J is naphthyl, benzothienyl, benzopyrrolyl, benzimidazolyl, indolyl each optionally substituted with one to three groups chosen from halogen, hydroxyl, cyano and $C_{1-6}$ linear or branched alkyl.

In another generic aspect of the invention, there is provided a compound of the formula (II):

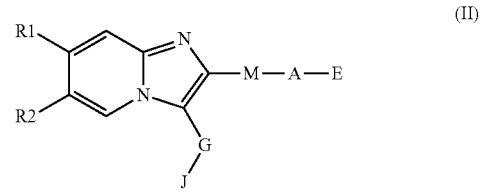

(II)

wherein for the Formula (II), the component

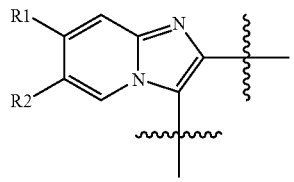

is chosen from A1-A8 in the table I below; in combination with any component

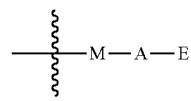

chosen from B1-B19 in the table I below; component

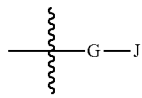

chosen from C1-C8 in the table I below;

TABLE I
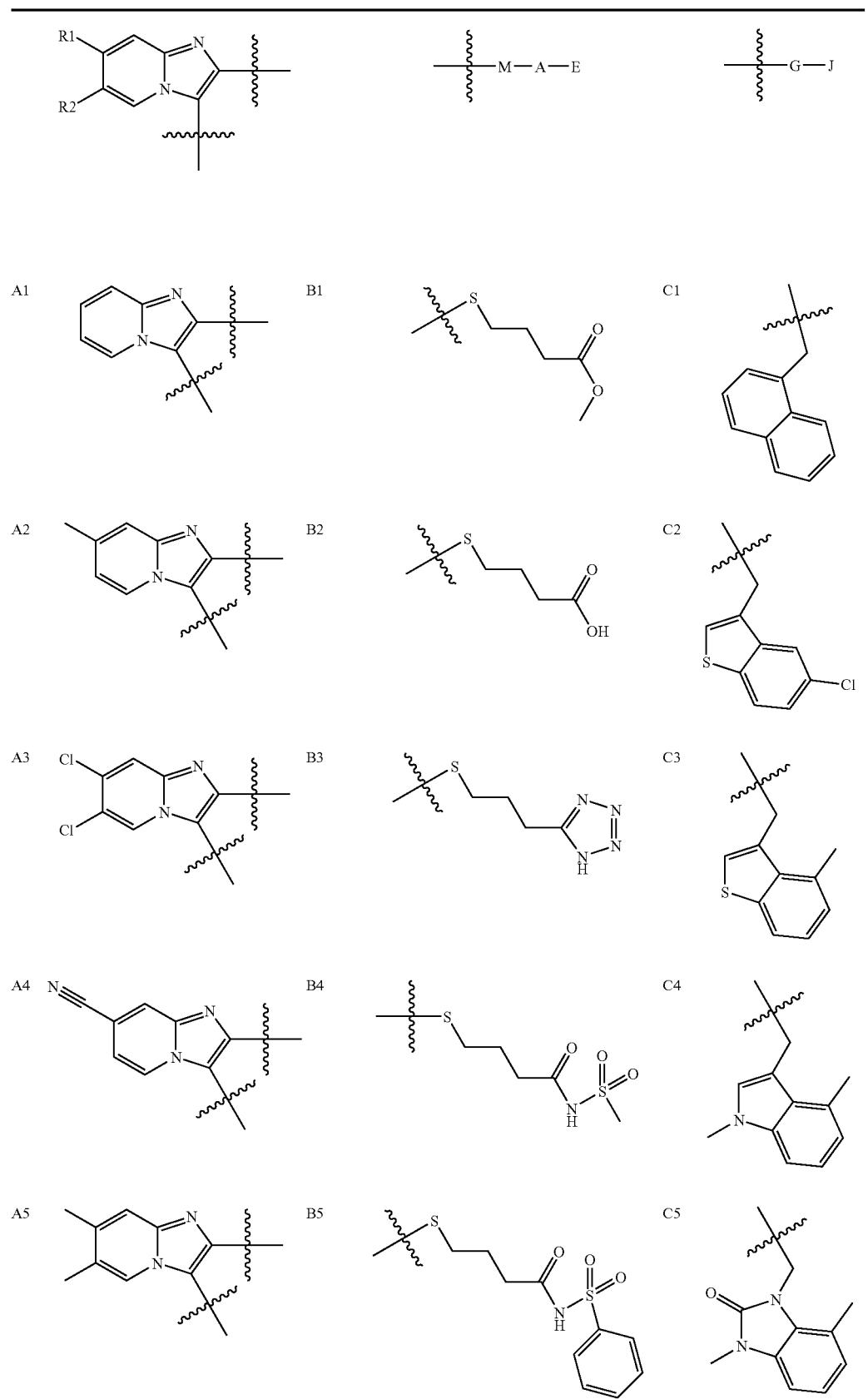

TABLE I-continued
| | | | | | |
|---|---|---|---|---|---|
| A6 | 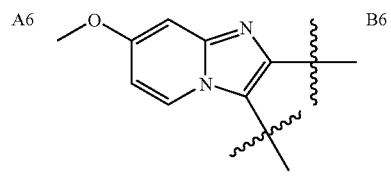 | B6 | 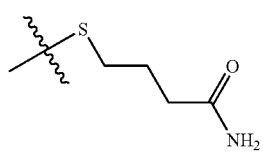 | C6 | 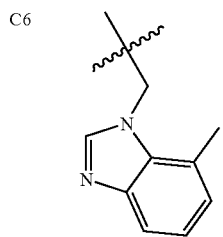 |
| A7 | 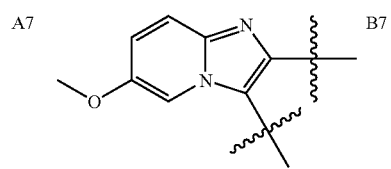 | B7 | 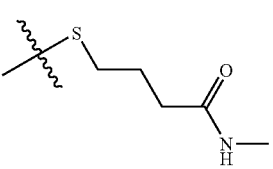 | C7 | 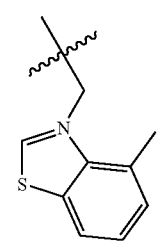 |
| A8 | 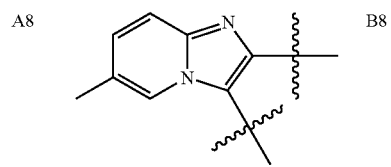 | B8 | 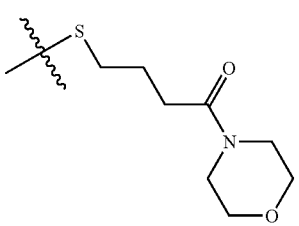 | C8 | 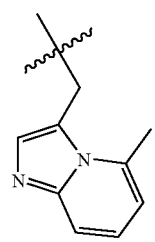 |
| | | B9 | 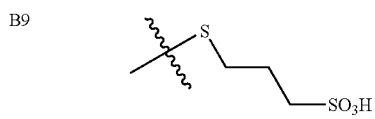 | | |
| | | B10 | 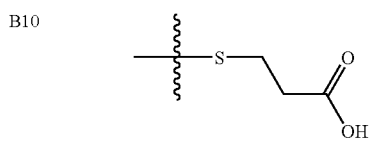 | | |
| | | B11 | 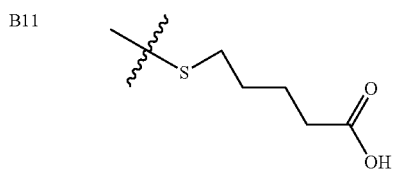 | | |
| | | B12 | 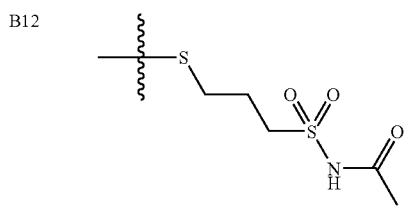 | | |

TABLE I-continued
B13 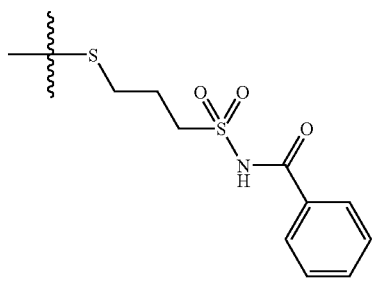
B14 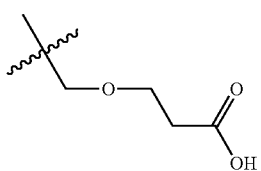
B15 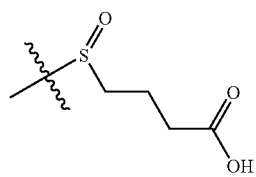
B16 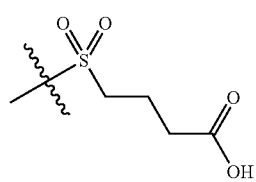
B17 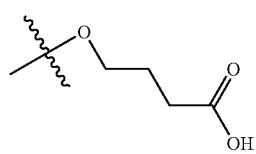

TABLE I-continued
B18 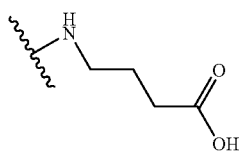
B19 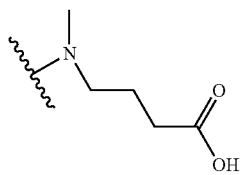
or the pharmaceutically acceptable salts thereof
In another generic aspect of the invention, there is provided a compound of the formula (III):
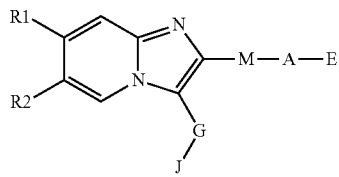
(III)
wherein for the Formula (III), the component
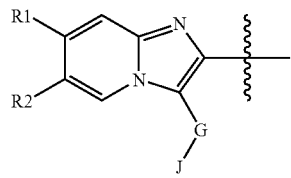
is chosen from A1-A15 in the table I below; in combination with any component
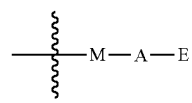
chosen from B1-B19 in the table II below;
TABLE II
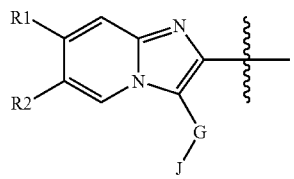     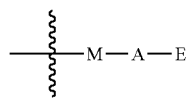
A1 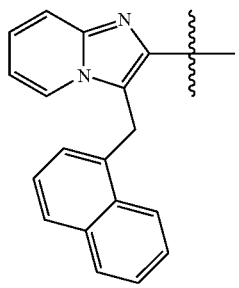     B1 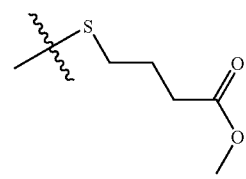

TABLE II-continued
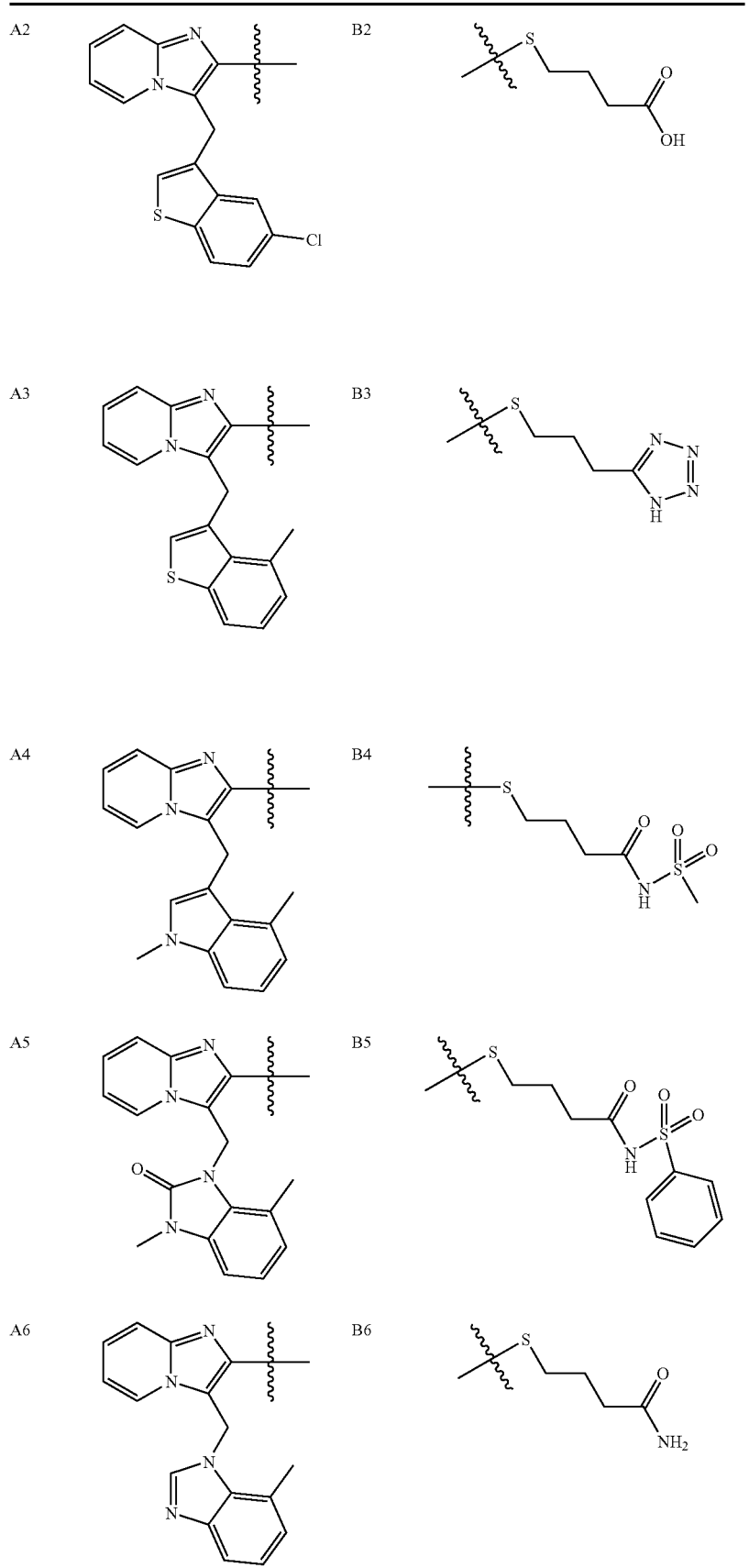

TABLE II-continued
| | | | |
|---|---|---|---|
| A7 | 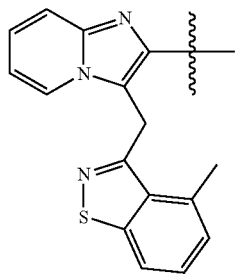 | B7 | 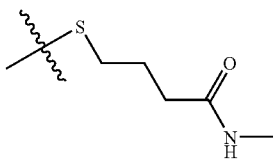 |
| A8 | 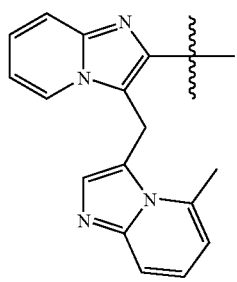 | B8 | 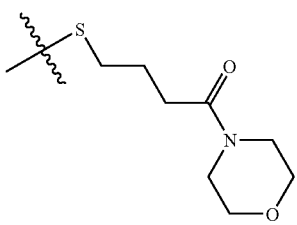 |
| A9 | 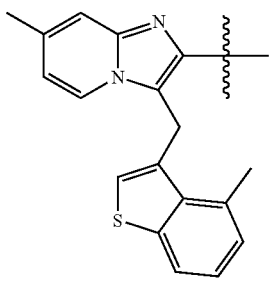 | B9 | 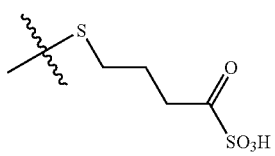 |
| A10 | 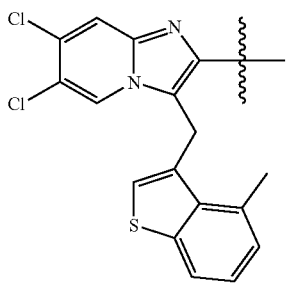 | B10 | 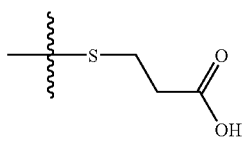 |
| A11 | 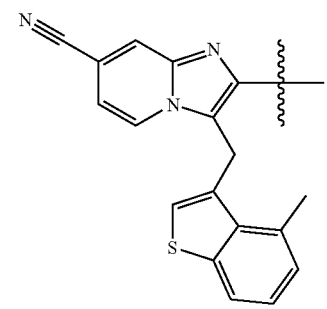 | B11 | 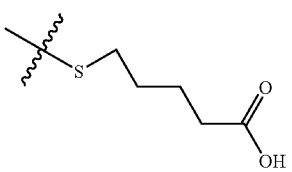 |

TABLE II-continued
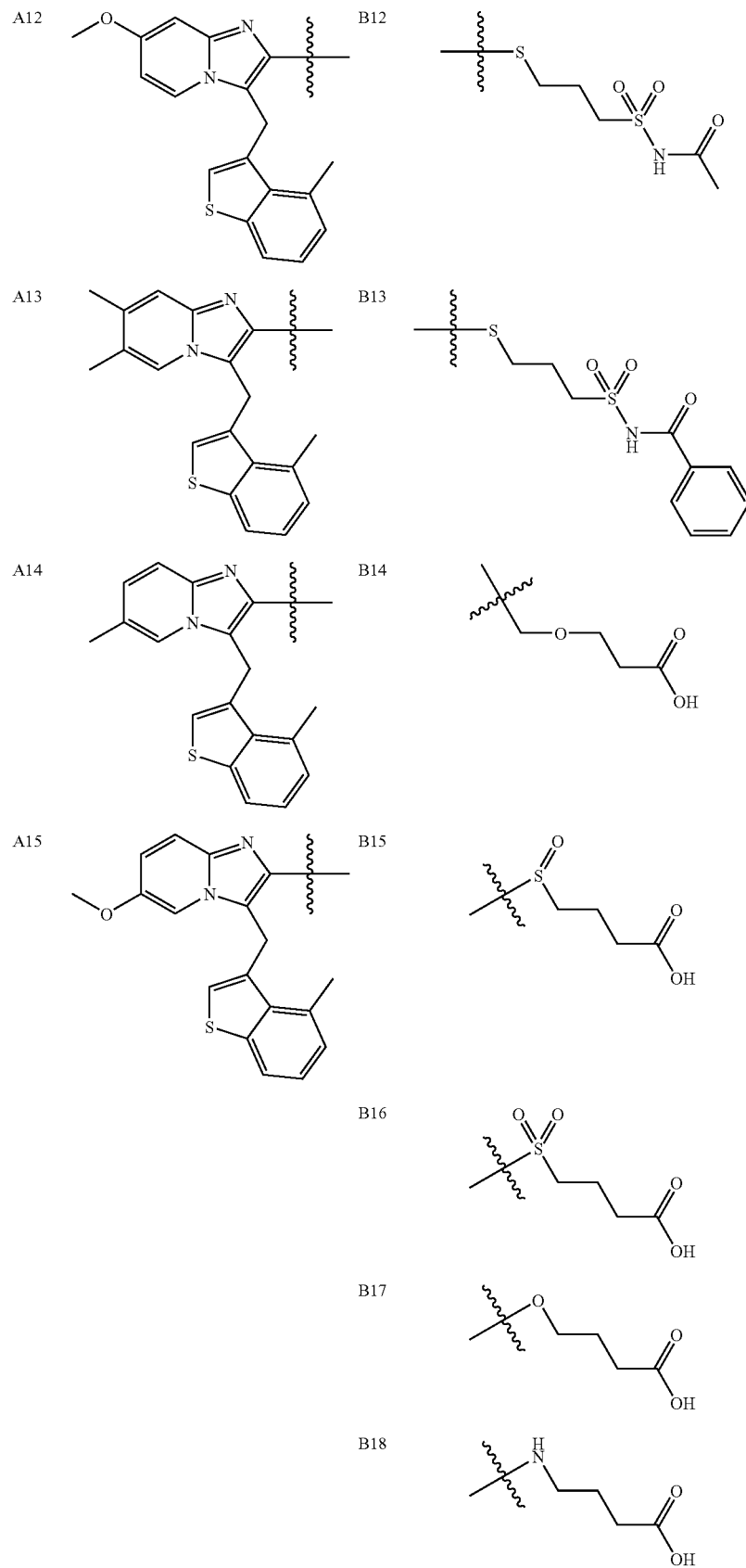

TABLE II-continued
B19 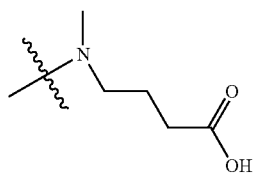
or the pharmaceutically acceptable salts thereof
In another embodiment of the invention there is provided the following compounds, in table III, which can be made according to the general synthetic procedures and examples which follow:
TABLE III
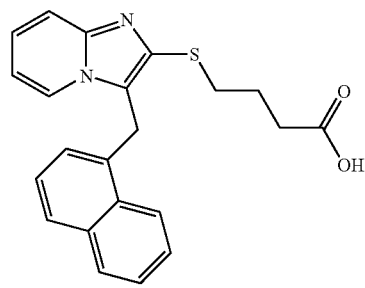
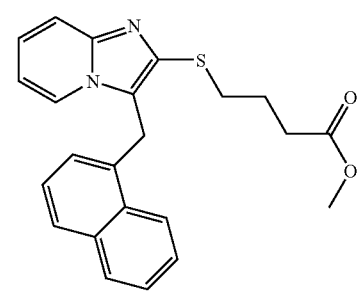
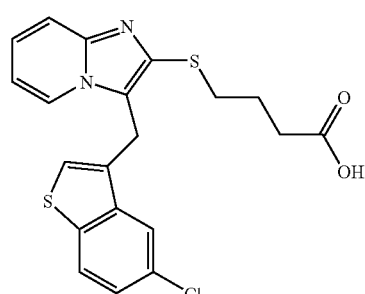
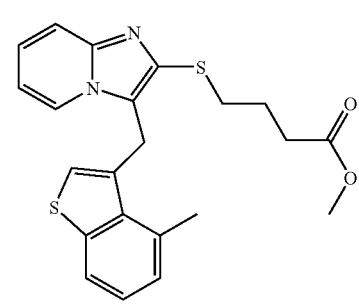
TABLE III-continued
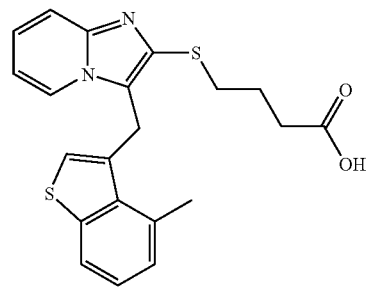
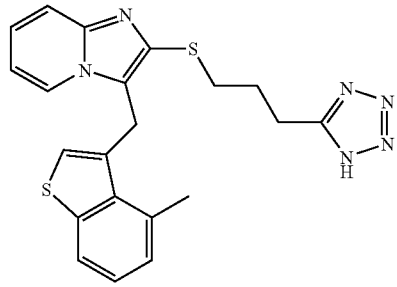
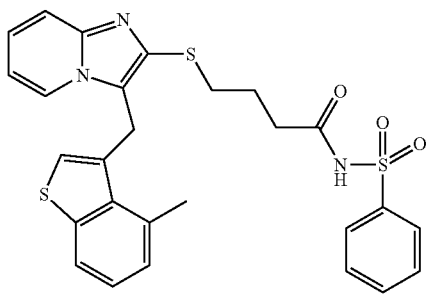
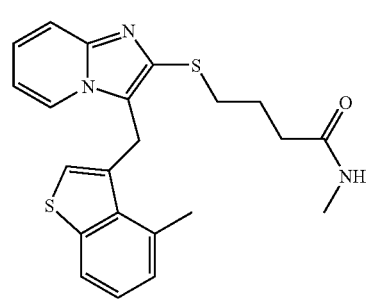

TABLE III-continued
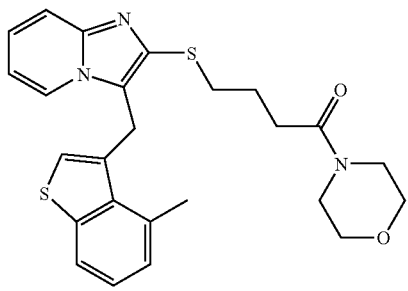
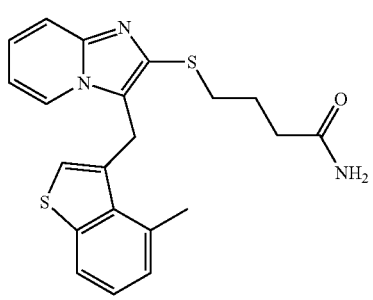
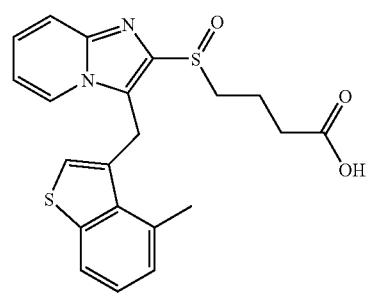
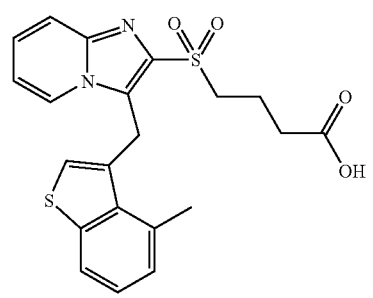
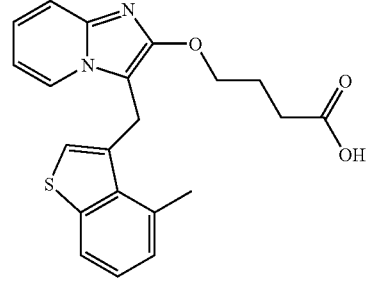
TABLE III-continued
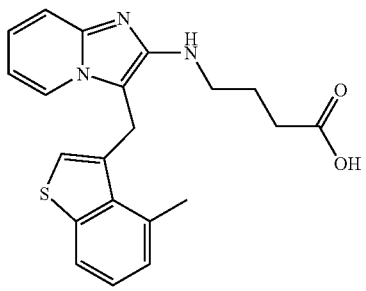
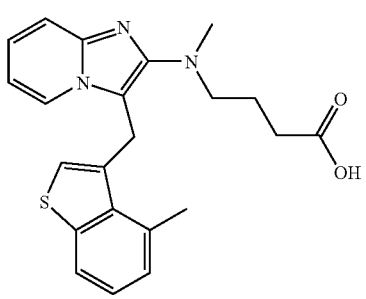
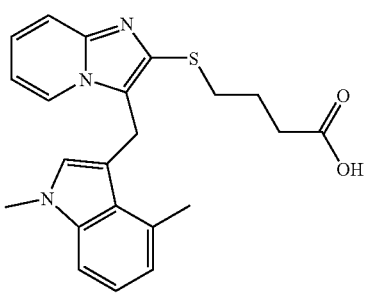
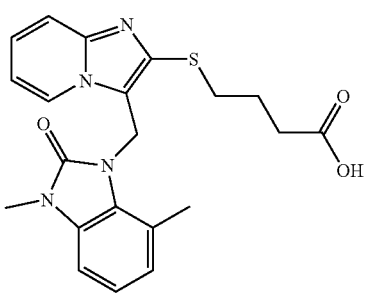
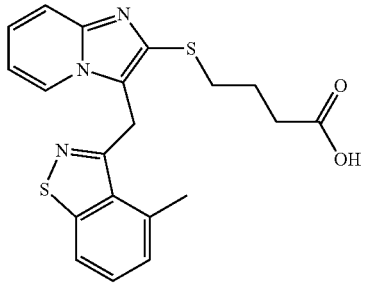

TABLE III-continued

TABLE III-continued

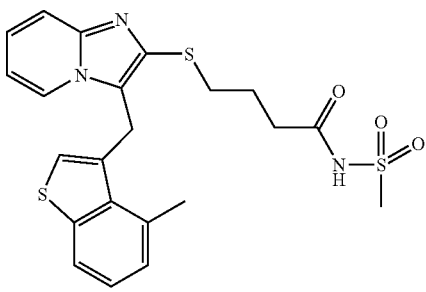

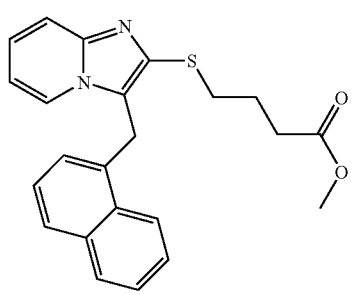

or the pharmaceutically acceptable salts thereof.

In another embodiment of the invention there is provided the following preferred compounds, in table IV, which can be made according to the general synthetic procedures and examples which follow:

TABLE IV

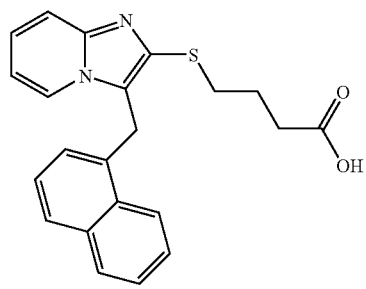

Chymase IC50 = 195 nM

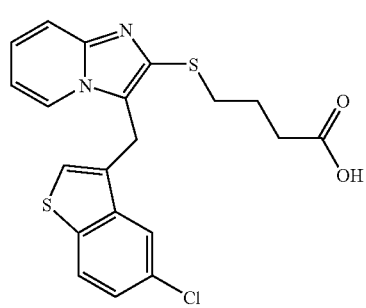

Chymase IC50 = 425 nM

TABLE IV-continued

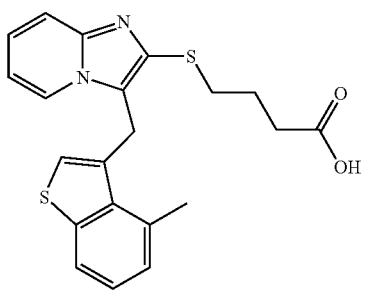

Chymase IC50 = 32 nM

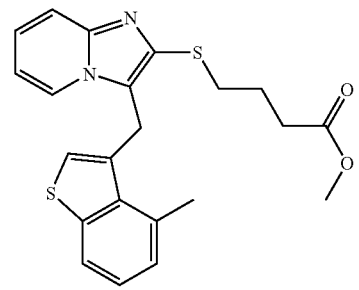

Chymase IC50 = 945 nM or the pharmaceutically acceptable salts thereof

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures, and individual diastereomers. All such isomeric forms of these compounds are expressly included in the present invention. Each stereogenic carbon may be in the R or S configuration, or a combination of configurations.

Some of the compounds of formula (I), (II) or (III) can exist in more than one tautomeric form. The invention includes methods using all such tautomers.

All terms as used herein in this specification, unless otherwise stated, shall be understood in their ordinary meaning as known in the art. For example, $C_{1-4}$alkoxy includes the organic radical $C_{1-4}$alkyl with a terminal oxygen, such as methoxy, ethoxy, propoxy, butoxy.

All organic radicals: alkyl, alkenyl and alkynyl groups, or such groups which are incorporated in other radicals such as acyl and alkoxy, shall be understood as being branched or unbranched where structurally possible and unless otherwise specified, and may be partially or fully halogenated.

The term "lower" referred to above and hereinafter in connection with organic radicals or compounds respectively defines such as branched or unbranched with up to and including 7, preferably up to and including 4 and advantageously one or two carbon atoms.

A cyclic group shall be understood to mean carbocycle, heterocycle or heteroaryl, each may be partially or fully halogenated.

An acyl group is a radical defined as —C(O)—R, where R is an organic radical or a cyclic group. Acyl represents, for example, carbocyclic or heterocyclic aroyl, cycloalkylcarbonyl, (oxa or thia)-cycloalkylcarbonyl, lower alkanoyl, (lower alkoxy, hydroxy or acyloxy)-lower alkanoyl, (mono- or dicarbocyclic or heterocyclic)-(lower alkanoyl or lower alkoxy-, hydroxy- or acyloxy-substituted lower alkanoyl), or biaroyl.

Carbocycles include hydrocarbon rings containing from three to fourteen carbon atoms. These carbocycles may be either aromatic either aromatic or non-aromatic ring systems. The non-aromatic ring systems may be mono- or polyunsaturated, monocyclic, bicyclic or tricyclic and may be bridged. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, benzyl, indanyl, indenyl, benzocyclobutanyl, dihydronaphthyl, tetrahydronaphthyl, naphthyl, decahydronaphthyl, benzocycloheptanyl, adamantyl, norbornyl, fluorene, and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or non-aromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxolanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N, O and S. Unless otherwise stated, such heteroaryls include aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzopyrrolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, tetrazol-5-yl, 5-oxo-1,2,4-oxadiazol-3-yl, 5-oxo-1,2,4-thiadiazol-3-yl, 5-thioxo-1,2,4-oxadiazol-3-yl, 5-thioxo-1,2,4-thiadiazol-3-yl, 3-oxo-1,2,4-oxadiazol-5-yl, N3,5-dioxo-5-oxadiazolidino, 2-oxo1,3,4-oxadiazol-2-yl, 3-oxo1,2,4-triazol-5-yl, 2,dioxo-benzothiadiazin-6-yl, 1,2-dioxo-3-hydroxy-3-cyclobuten-4-yl, and imidazo[4,5-b]pyridinyl.

The term "heteroatom" as used herein shall be understood to mean atoms other than carbon such as oxygen, nitrogen, sulfur and phosphorous.

As used herein, "nitrogen" and "sulfur" include any oxidized form of nitrogen and sulfur and the quaternized form of any basic nitrogen. All heteroatoms in open chain or cyclic radicals include all oxidized forms.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative and/or is partially or fully halogenated. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be $-CH_2CHF_2$, $-CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I), (II) or (III). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof A pharmacologically active metabolite shall be understood to mean any compound of the invention capable of being metabolized enzymatically or chemically. This includes, for example, hydroxylated or oxidized derivative compounds of the formula (I), (II) or (III).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4$ alkyl$)_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds described herein are either commercially available or can be made by methods and any necessary intermediates well known in the art.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention also provides processes for making compounds of Formula (I), (II) and (III). In all schemes, unless specified otherwise, R1, R2, A, E, G, M and J in the formulas below shall have the meaning of R1, R2, A, E, G, M and J in Formula (I), (II) and (III) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization. The appropriately substituted starting materials and intermediates used in the preparation of compounds of the invention are either commercially available or readily prepared by methods known in the literature to those skilled in the art, and are illustrated in the synthetic examples below.

Compounds of Formula (I), (II) and (III) may be synthesized by the method illustrated in Scheme 1

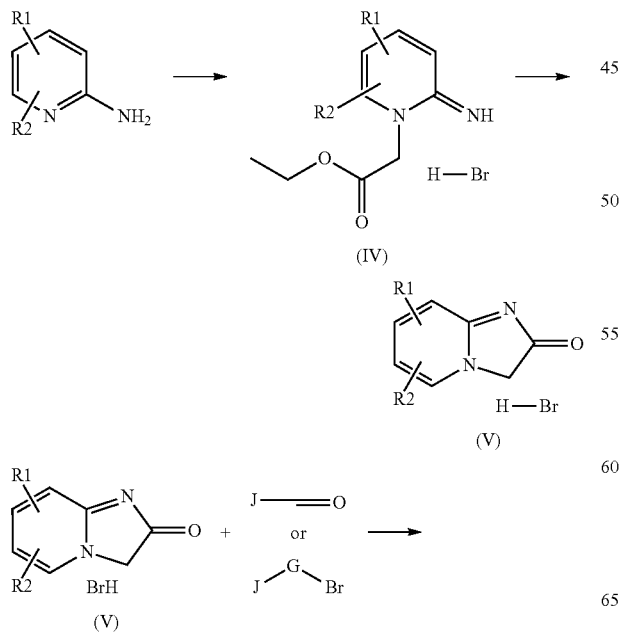

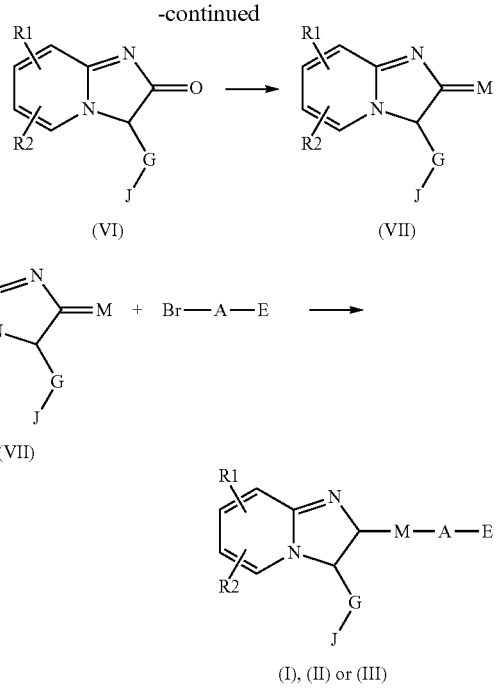

Reaction of an optionally substituted 2-amino pyridine with ethylbromoacetate in a suitable solvent provides an imino pyridinyl compound of formula (IV). Cyclization of the imino pyridinyl compound, by heating in a suitable solvent, provides an intermediate imidazo pyridinone of formula (V). Reacting the intermediate of formula (V) with an aldehyde J-CHO, followed by reduction using a suitable reducing agent, provides an alkylated intermediate of formula (VI) wherein G=CH₂. Alternatively, alkylation of the intermediate (V) with a suitable alkylating agent J-G-Br provides the intermediate of formula (VI). Reacting the intermediate of formula (VI) with a suitable reagent, such as Lawesson's reagent, in a suitable solvent, provides a thione of formula (VII). Reaction of the intermediate thione of formula (VII) with Br-A-E, in a suitable solvent, provides compounds of formula (I), (II) or (III).

Further modification of the initial product of formula (I) or (II) by methods known in the art and illustrated in the Examples below, may be used to prepare additional compounds of this invention.

EXAMPLE 1

Synthesis of 4-(3-Naphthalen-1-ylmethyl-2,3-dihydro-imidazo[1,2-a]pyridin-2-ylsulfanyl)-butyric acid Synthesis of imidazo[1,2-a]pyridin-2-one hydrobromide salt

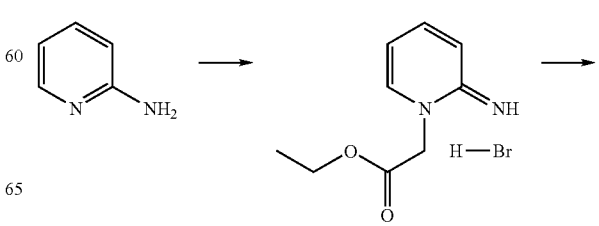

-continued

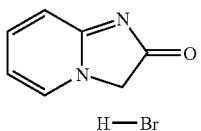

(2-Imino-2H-pyridin-1-yl)-acetic acid ethyl ester hydrobromide salt

To 39 mL (0.35 mol) of ethyl bromoacetate is added 9.4 g (0.1 mol) of 2-aminopyridine portionwise at 0° C. The resulting mixture is allowed to warm to room temperature and stirred at this temperature for 30 minutes. The precipitate is collected and washed with hexane to give the desired compound as light tan solid.

Imidazo[1,2-a]pyridin-2-one hydrobromide salt

A solution of 9 g (34.4 mmol) of (2-imino-2H-pyridin-1-yl)-acetic acid ethyl ester hydrobromide salt in 200 mL of ethanol is heated at reflux for 18 h. The reaction mixture is then cooled to room temperature and the precipitate is collected. The isolated solid is washed with ethanol to give the desired compound.

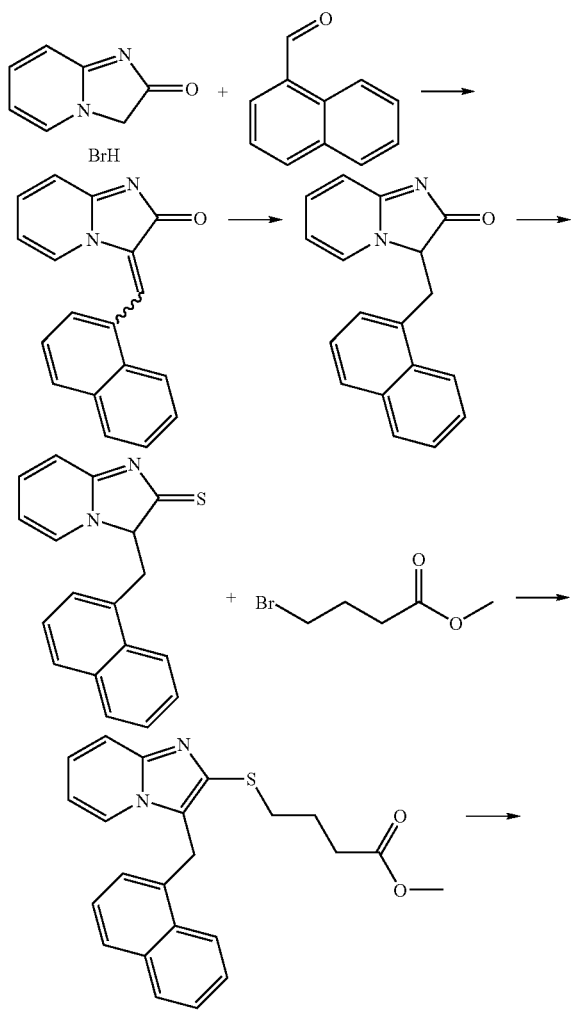

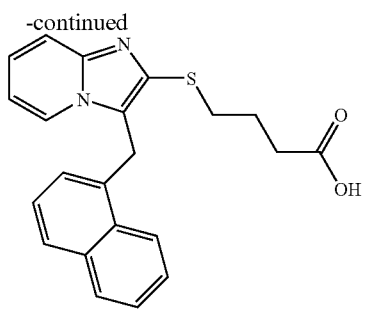

3-[1-Naphthalen-1-yl-meth-ylidene]-imidazo[1,2-a]pyridin-2-one

A mixture of 1 g (4.7 mmol) of imidazo[1,2-a]pyridin-2-one hydrobromide salt and 726 mg (4.7 mmol) of 1-naphthaldehyde in 20 mL of ethanol is heated at reflux for 1 h and then cooled to room temperature. The precipitate is collected. The isolated solid is suspended in 40 mL of 2M potassium carbonate solution and the resulting mixture is stirred for 48 h at room temperature. The precipitated solid is collected and washed with water to give the desired compound.

3-Naphthalen-1-ylmethyl-imidazo[1,2-a]pyridin-2-one

To a suspension of 137 mg (3.7 mmol) of sodium borohydride in 15 mL of ethanol is added a solution of 500 mg (1.8 mmol) of 3-[1-naphthalen-1-yl-methylidene]-imidazo[1,2-a]pyridin-2-one in 50 mL of methanol, dropwise at −78° C. After stirring for 10 min at −78° C., the reaction mixture is quenched with saturated aqueous ammonium chloride solution at −78° C. The product is extracted with dichloromethane. The organic layer is dried over magnesium sulfate, filtered and concentrated in vacuo to give the desired compound.

3-Naphthalen-1-ylmethyl-imidazo[1,2-a]pyridine-2-thione

A suspension of 200 mg (0.73 mmol) of 3-naphthalen-1-ylmethyl-imidazo[1,2-a]pyridin-2-one and 250 mg (0.62 mmol) of 2,4-bis-(4-methoxyphenyl)-1,3-dithia-2,4-diphosphetane 2,4-disulfide (Lawesson's reagent) in 20 mL of toluene is heated at 160° C. for 1 h under microwave condition. The resulting mixture is dissolved in methanol and absorbed on silica gel. The slurry is dried under reduced pressure and is purified by flash chromatography on silica gel. The compound is eluted 5~10% methanol in dichloromethane solution to give the desired compound.

4-(3-Naphthalen-1-ylmethyl-2,3-dihydro-imidazo[1,2-a]pyridin-2-ylsulfanyl)-butyric acid methyl ester A mixture of 75 mg (0.26 mmol) of 3-naphthalen-1-ylmethyl-imidazo[1,2-a]pyridine-2-thione and 70 mg (0.39 mmol) of methyl 4-bromobutyrate and 72 mg (0.52 mmol) of potassium carbonate in 3 mL of 50% acetone in dichloromethane is stirred at room temperature for 18 h. The mixture is concentrated in vacuo and the residue is purified by flash chromatography on silica gel eluting with 50~75% ethyl acetate in hexanes to give the desired compound.

4-(3-Naphthalen-1-ylmethyl-2,3-dihydro-imidazo[1,2-a]pyridin-2-ylsulfanyl)-butyric acid A solution of 50 mg (0.13 mmol) of 4-(3-naphthalen-1-ylmethyl-2,3-dihydro-imidazo[1,2-a]pyridin-2-ylsulfanyl)-butyric acid methyl ester in 2 mL of THF is treated with a solution of 11 mg (0.26 mmol) of lithium hydroxide monohydrate in 1 mL of water at room temperature. The resulting mixture is heated to 40° C., and stirred at this temperature for 3 h. Then the reaction mixture is cooled to room temperature and concentrated in vacuo. The residue is diluted with water and neutralized with 1N HCl solution. The product is extracted with ethyl acetate, and the organic layer is separated. The organic layer is washed with water and brine, dried over magnesium sulfate, filtered and concentrated in vacuo. The residue is purified by flash chromatography eluting with 3~10% methanol in dichloromethane solution to give the title compound. LCMS (ESMS): m/z 377 (M+H$^+$)

EXAMPLE 2

Synthesis of 4-[3-(4-Methyl-benzo[b]thiophen-3-ylmethyl)-imidazo[1,2-a]pyridin-2-ylsulfanyl]-butyric acid

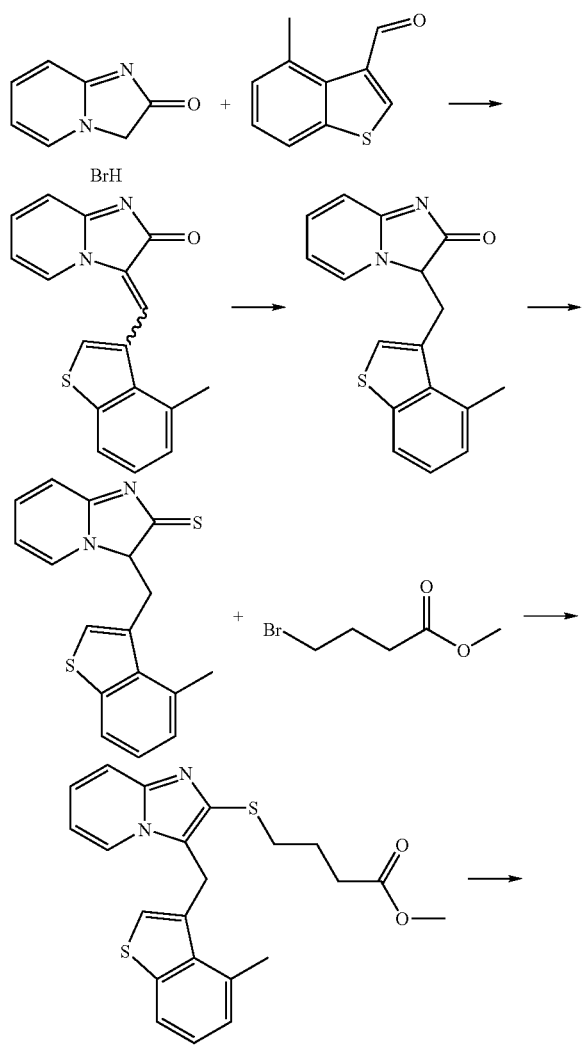

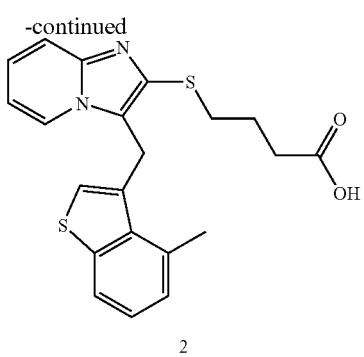

2

3-(4-Methyl-benzo[b]thiophen-3-ylmethylene)-imidazo[1,2-a]pyridin-2-one

A mixture of 1.6 g (7.4 mmol) of imidazo[1,2-a]pyridin-2-one hydrobromide salt and 1.2 g (6.7 mmol) of 4-methyl-benzo[b]thiophene-3-carbaldehyde in 40 mL of ethanol is heated at reflux for 1 h and then cooled to room temperature. The precipitate is collected. The isolated solid is suspended in 40 mL of 2M potassium carbonate solution and the resulting mixture is stirred for 48 h at room temperature. The solid is collected and washed with water to give the desired compound.

3-(4-Methyl-benzo[b]thiophen-3-ylmethyl)-imidazo[1,2-a]pyridin-2-one

To a suspension of 121 mg (3.2 mmol) of sodium borohydride in 50 mL of ethanol is added a solution of 624 mg (2.1 mmol) of 3-(4-methyl-benzo[b]thiophen-3-ylmethylene)-imidazo[1,2-a]pyridin-2-one in 50 mL of methanol dropwise at −78° C. After stirring for 15 minutes at −78° C., the reaction mixture is quenched with saturated aqueous ammonium chloride solution at −78° C. The product is extracted with dichloromethane. The organic layer is dried over magnesium sulfate, filtered and concentrated in vacuo to give the desired compound.

3-(4-Methyl-benzo[b]thiophen-3-ylmethyl)-imidazo[1,2-a]pyridine-2-thione

A suspension of 475 mg (1.6 mmol) of 3-(4-methyl-benzo[b]thiophen-3-ylmethyl)-imidazo[1,2-a]pyridin-2-one and 525 mg (1.3 mmol) of 2,4-bis-(4-methoxyphenyl)-1,3-dithia-2,4-diphosphetane 2,4-disulfide in 20 mL of toluene is heated at 170° C. for 90 minutes under microwave condition. The precipitated solid is collected to give the desired compound.

4-[3-(4-Methyl-benzo[b]thiophen-3-ylmethyl)-imidazo[1,2-a]pyridin-2-ylsulfanyl]-butyric acid methyl ester A mixture of 472 mg (1.5 mmol) of 3-(4-methyl-benzo[b]thiophen-3-ylmethyl)-imidazo[1,2-a]pyridine-2-thione and 407 mg (2.3 mmol) of methyl 4-bromobutyrate and 415 mg (3.0 mmol) of potassium carbonate in 5 mL of DMF is stirred at room temperature for 18 h. The mixture is diluted with water and the product is extracted with ethyl acetate. The organic layer is washed with water and brine, dried over magnesium sulfate, filtered and concentrated in vacuo. The residue is purified by flash chromatography on silica gel eluted with 1~5% methanol in dichloromethane to give the desired compound.

4-[3-(4-Methyl-benzo[b]thiophen-3-ylmethyl)-imidazo[1,2-a]pyridin-2-ylsulfanyl]-butyric acid A solution of 100 mg (0.24 mmol) of 4-[3-(4-methyl-benzo[b]thiophen-3-ylmethyl)-imidazo[1,2-a]pyridin-2-ylsulfanyl]-butyric acid methyl ester in 2 mL of THF is treated with a solution of 20 mg (0.48 mmol) of lithium hydroxide monohydrate in 1 mL of water at room temperature. The resulting mixture is heated to 40° C., and stirred at this temperature for 3 h. The reaction mixture is then cooled to room temperature and concentrated in vacuo. The residue is diluted with water and neutralized with 1N HCl solution. The product is extracted with ethyl acetate, and the organic layer is separated. The organic layer is washed with water and brine, dried over magnesium sulfate, filtered and concentrated in vacuo. The residue is purified by flash chromatography eluting with 3~10% methanol in dichloromethane solution to give the title compound. LCMS (ESMS): m/z 397 (M+H$^+$)

EXAMPLE 3

Synthesis of 4-[3-(5-Chloro-benzo[b]thiophen-3-ylmethyl)-imidazo[1,2-a]pyridin-2-ylsulfanyl]-butyric acid

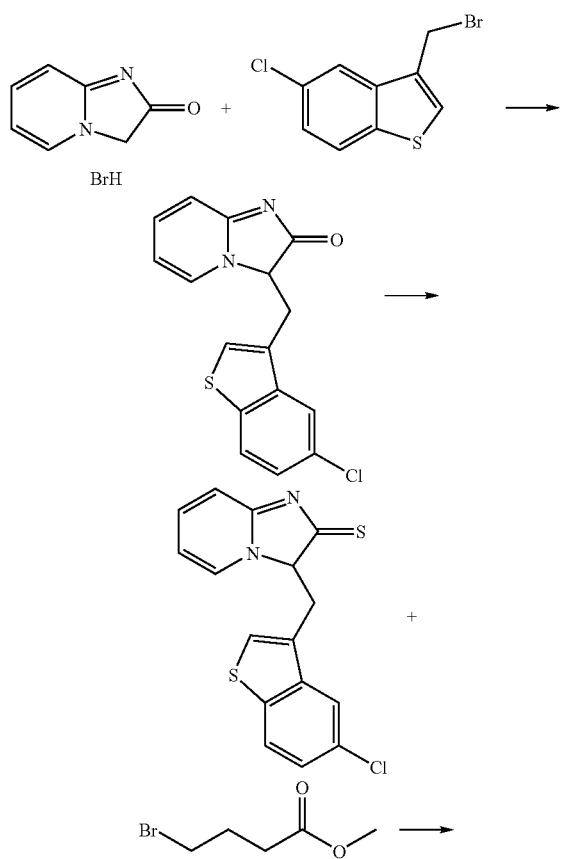

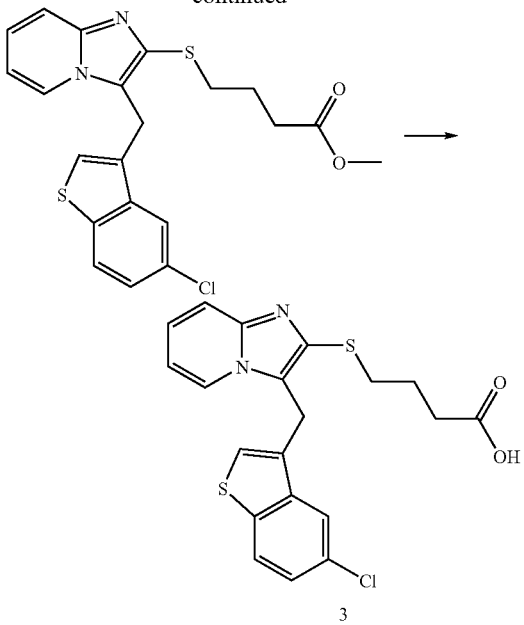

3-(5-Chloro-benzo[b]thiophen-3-ylmethyl)-imidazo[1,2-a]pyridin-2-one

A mixture of 100 mg (0.47 mmol) of imidazo[1,2-a]pyridin-2-one hydrobromide salt and 122 mg (0.47 mmol) 3-bromomethyl-5-chloro-benzo[b]thiophene in 5 mL of THF is treated with 1 mL (1.0 mmol) of 1M lithium bis(trimethylsilyl)amide THF solution at −78° C. The resulting mixture is stirred this temperature for 1 h and the mixture is quenched with saturated ammonium chloride solution. The product is extracted with ethyl acetate. The organic layer is washed with water and brine, dried over sodium sulfate, filtered and concentrated in vacuo. The residue is purified by flash chromatography to give the desired compound.

3-(5-Chloro-benzo[b]thiophen-3-ylmethyl)-imidazo[1,2-a]pyridine-2-thione

A suspension of 172 mg (0.55 mmol) of 3-(5-chloro-benzo[b]thiophen-3-ylmethyl)-imidazo[1,2-a]pyridin-2-one and 110 mg (0.27 mmol) of 2,4-bis-(4-methoxyphenyl)-1,3-dithia-2,4-diphosphetane 2,4-disulfide in 20 mL of toluene is heated at 160° C. for 90 min under microwave condition. The resulting mixture is concentrated in vacuo and the residue is purified by flash chromatography to give the desired compound.

4-[3-(5-Chloro-benzo[b]thiophen-3-ylmethyl)-imidazo[1,2-a]pyridin-2-ylsulfanyl]-butyric acid methyl ester A mixture of 60 mg (0.18 mmol) of 3-(5-chloro-benzo[b]thiophen-3-ylmethyl)-imidazo[1,2-a]pyridine-2-thione and 38 mg (0.21 mmol) of methyl 4-bromobutyrate and 58 mg (0.42 mmol) of potassium carbonate in 2 mL of DMF is stirred at room temperature for 18 h. The mixture is diluted with water and the product is extracted with ethyl acetate. The organic layer is washed with water and brine, dried over magnesium sulfate, filtered and concentrated in vacuo. The residue is purified by flash chromatography on silica gel eluted with 1~5% methanol in dichloromethane to give the desired compound.

4-[3-(5-Chloro-benzo[b]thiophen-3-ylmethyl)-imidazo[1,2-a]pyridin-2-ylsulfanyl]-butyric acid A solution of 15 mg (0.04 mmol) of 4-[3-(5-chloro-benzo[b]thiophen-3-ylmethyl)-imidazo[1,2-a]pyridin-2-ylsulfanyl]-butyric acid methyl ester in 2 mL of THF is treated with a solution of 10 mg (0.24 mmol) of lithium hydroxide monohydrate in 1 mL of water at room temperature. The resulting mixture is heated to 50° C., and stirred at this temperature for 2 h. The reaction mixture is then cooled to room temperature and concentrated in vacuo. The residue is purified by preparative TLC on silica gel to give the title compound. LCMS (ESMS): m/z 417 (M+H$^+$).

Methods of Use

In accordance with the invention, there are provided methods of using the compounds as described herein and their pharmaceutically acceptable derivatives. The compounds used in the invention inhibit Chymase. Since Chymase is known to transform angiotensin I to angiotensin II and may contribute to activation of TGF-β, matrix proteases and cytokines, the inhibition of Chymase is an attractive means for preventing and treating a variety of diseases or conditions. Examples include heart failure including chronic heart failure (non-ischemic), post-myocardial infarction heart failure (ischemic), acute myocardial infarction, reperfusion injury, left ventricular dysfunction, cardiac fibrosis, diastolic heart failure and hypertrophic cardiomyopathy, hypertension including pulmonary hypertension, systolic hypertension and resistant hypertension, including coronary artery disease, peripheral arterial occlusive disease, aneurism, stable/unstable angina, restenosis, diabetic nephropathy, atrial fibrillation/ventricular arrhythmias, valvular heart disease, pericardial diseases, renal insufficiency (chronic kidney disease, end stage renal disease), stroke. The compounds of the invention may also be useful for the following procedures: coronary artery bypass grafting, percutaneous coronary intervention and stenting.

Other diseases within the scope of the invention include allergic rhinitis, dermatitis, asthma, chronic obstructive pulmonary disease (COPD), and pulmonary inflammation, asthma, osteoarthritis, bone resorption diseases, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, inflammatory bowel diseases, acute and chronic pain as well as symptoms of inflammation, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopheresis, granulocyte transfusion associated syndromes, and necrotizing enterocolitis, traumatic arthritis, and sepsis. Reference in this regard may be made to U.S. Pat. No. 5,948,785; U.S. Pat. No. 6,271,238; U.S. Pat. No. 5,691,335; U.S. Pat. No. 5,814,631; U.S. Pat. No. 6,300,337; EP 1,099,690; U.S. Pat. No. 6,323,219; US 2005-0245536 A1; Fukami, et al., *Current Pharmaceutical Design* 1998, vol. 4, pp. 439-453.

As disclosed in the Background of the Invention, the compounds of the invention may contribute to activation of cytokines, they will therefore be useful for treating oncological diseases. Reference in this regard may be made to US 2005-0245536 A1. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophthalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds described herein may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Combinations with other therapeutics include but are not limited to: angiotensin II receptor blockers, angiotensin converting enzyme inhibitors, CETP inhibitors/apoA1 mimetics, adenosine diphosphate (P2Y12) inhibitors, direct thrombin inhibitors, aldosterone antagonists, factor Xa inhibitors, natriuretic peptides (ANP/BNP), renin inhibitors, anti-arrhythmics, Chymase inhibitors, HMG-CoA Reductase inhibitors (Statins), Rho kinase inhibitors, beta-blockers, Lipoprotein-associated phospholipase A2 inhibitors, cardiac glycosides, calcium channel blockers, diuretics, fibrates, Endothelin Receptor Antagonists, GPIIb/IIIa inhibitors, histone deacetylase inhibitors, heparins, nicotinic acid derivatives, vasopeptidase inhibitors, nitrites and nitrates, fatty acid oxidation inhibitors, oral anticoagulants, acyl-CoA:cholesterol acyltransferase inhibitors, thrombolytics, microsomal triglyceride transfer protein inhibitors, thiazolidinediones, adenosine receptor modulators, cholesterol absorption inhibitors, Advanced Glycation End products/receptor (AGE/RAGE) interaction modulators/blockers, acetyl salicylic acid, dipyridamole, gene therapy and cell therapy.

Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the above-described compounds include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:
  (i) preventing the disease-state from occurring in a patient, in particular, when such patient is genetically or otherwise predisposed to the disease-state but has not yet been diagnosed as having it;
  (ii) inhibiting or ameliorating the disease-state in a patient, i.e., arresting or slowing its development; or
  (iii) relieving the disease-state in a patient, i.e., causing regression or cure of the disease-state.

In Vitro Assay for Inhibition of Chymase

Chymase assays were performed in a total volume of 15 µL in Corning black opaque 384-well microtiter plates with a non-binding surface (Corning, N.Y.). The assay buffer was comprised of 20 mM Tris HCl pH 8.0, 50 mM NaCl, 0.01% CHAPS. The test compounds were serially diluted 3-fold with neat DMSO in a 96-well polypropylene plate from a 10 mM DMSO stock to give the 10 point dose response curve. 3 µL of the resulting DMSO solution were transferred to a 384-well polypropylene plate in duplicate, and 37 µL of assay buffer was added. Chymase was added to the assay plate in 3 uL of assay buffer followed by 2 uL of the appropriate compound dilution using a PlateMate Plus (Matrix Technologies Corp., Hudson, N.H.). The reaction was initiated by the addition of 10 uL rhodamine 110, bis-(succinoyl-L-alanyl-L-alanyl-L-prolyl-L-phenylalanylamide) (American Peptides, Sunnyvale, Calif.) in assay buffer containing 150 µM tris(2-carboxyethyl)phosphine (TCEP, Pierce Chemical, Rockford, Ill.) using a Multidrop (Thermo Electron Corp., Waltham, Mass.). Final assay concentrations were 500 pM chymase, 100 nM substrate, 100 µM TCEP, and 1% DMSO. The plates were incubated at 28° C. and 80% humidity for 1 hour, at which time the fluorescence was read on a Viewlux 1430 Microplate Imager (Perkin Elmer Life Sciences, Boston, Mass.) with 485 nm excitation, 530 nm emission, and a fluorescein dichroic mirror. The percentage of control values were calculated relative to assay blanks containing complete reaction minus chymase and a 100% control containing assay buffer with 1% DMSO in place of compound. IC50 values were obtained by fitting the data using XLFit4 (IDBS Software). Preferred compounds of the invention have an activity of 1 microMolar or less.

All patent and literature references cited in this application are incorporated herein by reference in their entirety.

What is claimed:
1. A compound of the formula (I):

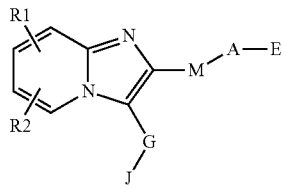

(I)

R1 and R2 are independently hydrogen, halogen, trihaloalkyl, trihaloalkoxy, cyano, hydroxyl, $C_{1-4}$ alkyl, $C_{1-4}$ alkoxy, —CORd, —COORd, —CON(Rc)Rd, —N(Rc)Rd, —N(Rc)CORd wherein each Rd is independently a hydrogen, $C_{1-6}$ linear or branched alkyl or cycloalkyl, $C_{1-6}$ linear or branched alkenyl or heterocyclyl or where R1 and R2 together represent —O—CH$_2$—O, —O—CH$_2$—CH$_2$—O— or —CH$_2$—CH$_2$—CH$_2$—, wherein each group is optionally independently substituted with one to three substituents chosen from $C_{1-4}$ acyl, $C_{1-4}$ alkyl, $C_{1-4}$ alkoxy, amino, dialkylamino, cyano, carboxy, carboxamido, halogen, hydroxyl and phenyl optionally substituted with halogens;

A is $C_1$-$C_7$ linear, branched or cyclic alkyl group optionally interrupted by one or more —O—, —S—, —SO—, and —SO$_2$— optionally substituted with one to three substituents chosen from halogen, $C_{1-6}$ linear or branched alkyl, $C_{1-6}$ linear or branched alkoxy, $C_{1-6}$ linear or branched alkylthio, $C_{1-6}$ linear or branched alkylsulfonyl, phenyl and oxo;

E is —COORe, —SO$_3$Re, —CONHRe, —SO$_2$NHRe, —NHSO$_2$Re, —CONHSO$_2$Re, —SO$_2$NH—CO(Rf), heteroaryl, heterocycyl, wherein each Re is independently hydrogen, $C_{1-4}$ alkyl or aryl, and Rf is $C_{1-4}$ alkyl or aryl;

G is $C_{1-6}$ linear or branched alkyl optionally interrupted by one or more of —O—, —S—, —SO$_2$ or —NRa—, wherein the alkyl group is optionally substituted with hydroxyl, cyano, $C_{1-6}$ linear or branched alkyl or $C_{1-6}$ linear or branched alkoxy;

M is a methylene group, oxygen, or —S(O)$_m$—, where m is an integer of 0-2; and, wherein the said methylene group is optionally substituted by one to two substituents chosen from hydroxyl, cyano, $C_{1-6}$ linear or branched alkyl, $C_{1-6}$ linear or branched alkoxy, trihalomethyl, trihalomethoxy, phenyl and oxo;

J is an optionally mono- or poly-substituted aromatic carbocycle or a heteroaromatic group having 4-10 carbon atoms containing one or more hetero atoms chosen from the group consisting of an oxygen atom, a nitrogen atom and a sulfur atom in its ring(s); each substituent on said aromatic or heteroaromatic groups is chosen from halogen, hydroxyl, cyano, $C_{1-6}$ linear or branched alkyl, $C_{1-6}$ linear or branched alkoxy, $C_{1-6}$ linear or branched alkylthio, $C_{1-6}$ linear or branched alkylsulfonyl, phenylsulfonyl, $C_{1-6}$ linear or branched acyl, $C_{1-6}$ linear or branched acylamino, trihalomethyl, trihalomethoxy, phenyl, oxo, —COORa, —CON(Rc)Ra, SO$_2$N(Rc)Ra, —N(Rc)Ra and phenoxy optionally substituted by one or more halogens;

Ra, and Rc are each independently C1-3 alkyl or hydrogen; or the pharmaceutically acceptable salts thereof.

2. The compound according to claim 1 and wherein:
R1 and R2 are attached as follows:

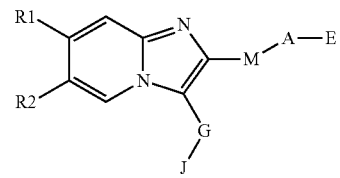

and are independently hydrogen, Cl, Br, F, I, trihaloalkyl, trihaloalkoxy cyano, hydroxyl, $C_{1-4}$ alkyl, $C_{1-4}$ alkoxy, —CORd, —COORd, —CON(Rc)Rd, —N(Rc)Rd, —N(Rc)CORd wherein each Rd is independently a hydrogen, $C_{1-6}$ linear or branched alkyl or cycloalkyl, $C_{1-6}$ linear or branched alkenyl or heterocyclyl chosen from pyrrole, pyrrolidinyl, pyrazole, imidazole, furan, tetrahydrofuran, oxazole, thiophene, tetrahydrothiophene and thiazole wherein for each ring possessing a sulfur heteroatom the sulfur is —S—, —S(O)— or —S(O)$_2$—, or where R1 and R2 together represent —O—CH$_2$—O, —O—CH$_2$—CH$_2$—O— or —CH$_2$—CH$_2$—CH$_2$—, wherein each group is optionally independently substituted with one to three substituents chosen from $C_{1-4}$ acyl, $C_{1-4}$ alkyl, $C_{1-4}$ alkoxy, amino, dialkylamino, cyano, carboxy, carboxamido, Cl, Br, F, I, hydroxyl and phenyl optionally substituted with one to three Cl, Br, F, I;

A is $C_1$-$C_7$ linear, branched optionally independently substituted with one to three substituents chosen from amino, cyano, carboxy, carboxamido, halogen, hydroxyl, nitro, phenyl, $C_{1-6}$ linear or branched alkyl and $C_{1-6}$ linear or branched alkoxy;

E is —COORe, —SO$_3$Re, —CONHRe, —CONHSO$_2$Re, —SO$_2$NH—CO(Rf), tetrazol-5-yl, 5-oxo-1,2,4-oxadiazol-3-yl, 5-oxo-1,2,4-thiadiazol-3-yl, 5-thioxo-1,2,4-oxadiazol-3-yl, 5-thioxo-1,2,4-thiadiazol-3-yl, 3-oxo-1,2,4-oxadiazol-5-yl, N3,5-dioxo-5-oxadiazolidino, 2-oxo-1,3,4-oxadiazol-2-yl, 3-oxo-1,2,4-triazol-5-yl or 2,dioxo-benzothiadiazin-6-yl, wherein each Re is independently hydrogen, $C_{1-4}$ alkyl or phenyl, and Rf is $C_{1-4}$ alkyl or aryl;

G is $C_{1-4}$ linear or branched alkyl optionally substituted with a substituent chosen from hydroxyl, a cyano, $C_{1-6}$ linear or branched alkyl and $C_{1-6}$ linear or branched alkoxy;

M is a methylene group, oxygen, or —S(O)$_m$—, where m is an integer of 0-2;

J is an optionally mono- or di-substituted phenyl, naphthyl, benzothienyl, benzopyrrolyl, benzimidazolyl, indolyl; each substituent on said aromatic or heteroaromatic groups is chosen from halogen, hydroxyl, cyano, $C_{1-4}$ linear or branched alkyl, $C_{1-4}$ linear or branched alkoxy, $C_{1-6}$ linear or branched alkylthio, $C_{1-6}$ linear or branched alkylsulfonyl, phenylsulfonyl, $C_{1-6}$ linear or branched acyl, $C_{1-6}$ linear or branched acylamino, trihalomethyl, trihalomethoxy, phenyl, oxo, —COORa, —CON(Rc)Ra, —SO$_2$N(Rc)Ra, N(Rc)Ra and phenoxy optionally substituted by one or more halogens.

3. The compound according to claim 2 and wherein:

R1 and R2 are independently hydrogen, Cl, F, trihalomethyl, trihalomethoxy, cyano, hydroxyl, $C_{1-2}$ alkyl, $C_{1-4}$ alkoxy, —CORd, —CON(Rc)Rd, —N(Rc)Rd, —N(Rc)CORd wherein each Rd is independently a hydrogen or $C_{1-6}$ linear or branched alkyl, $C_{1-6}$ linear or branched alkenyl, furan, tetrahydrofuran, thiophene and tetrahydrothiophene wherein for each ring possessing a sulfur heteroatom the sulfur is —S—, —S(O)— or —S(O)$_2$— or where R1 and R2 together represent —O—CH$_2$—CH$_2$—O—, wherein each group is optionally independently substituted with one to three substituents chosen from $C_{1-4}$ alkyl, $C_{1-4}$ alkoxy amino, cyano, carboxy, carboxamido, Cl, Br, F, I, and hydroxyl;

A is a —(CH$_2$)$_3$— group, optionally substituted with one substituent chosen from phenyl and $C_{1-3}$ alkyl;

E is —COORe wherein Re is hydrogen or methyl;

G is $C_{1-2}$ alkyl;

M is a methylene group, oxygen, or sulfur;

J is naphthyl, benzothienyl, benzopyrrolyl, benzimidazolyl, indolyl each optionally substituted with one to three groups chosen from halogen, hydroxyl, cyano and $C_{1-6}$ linear or branched alkyl.

4. A compound of the formula (II):

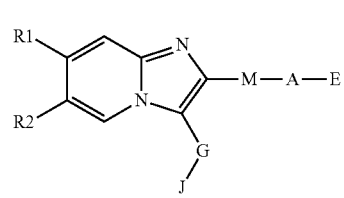

(II)

wherein for the formula (II), the component

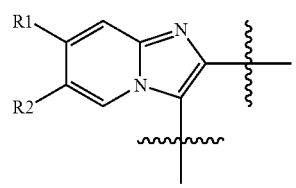

is chosen from A1-A8 in the table I below; in combination with any component

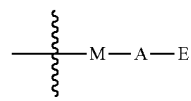

chosen from B1-B17 in the table I below; component

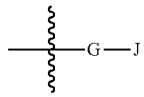

chosen from C1-C8 in Table I below;

TABLE I

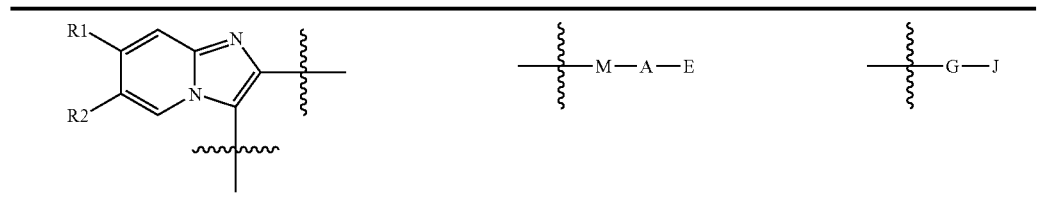

| A1 | B1 | C1 |
|---|---|---|
| 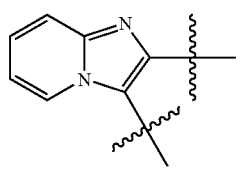 | 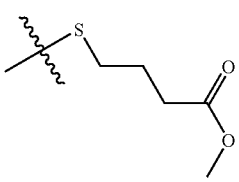 | 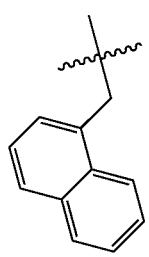 |

TABLE I-continued
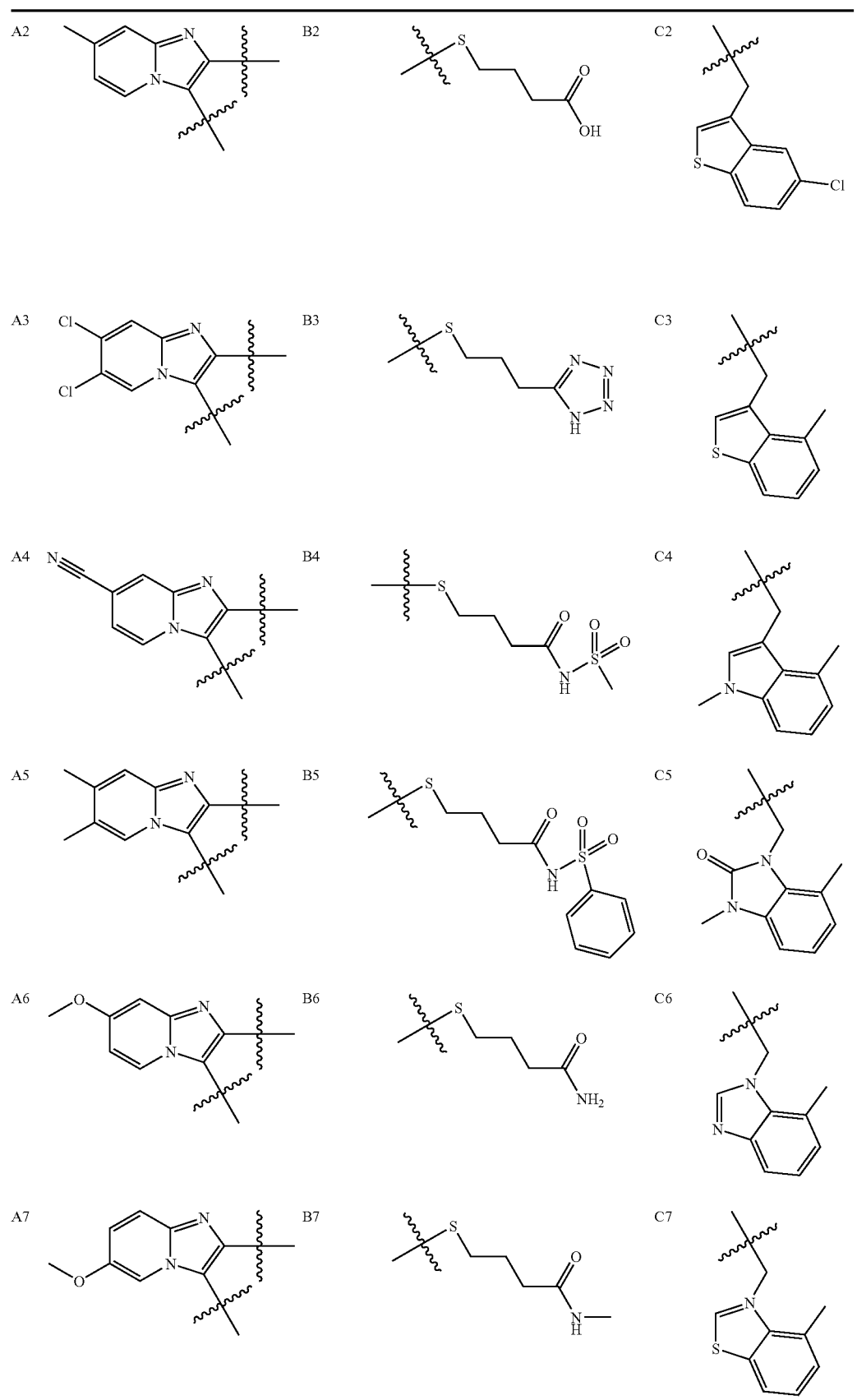

TABLE I-continued
| | | | | | |
|---|---|---|---|---|---|
| A8 | 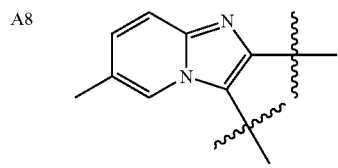 | B8 | 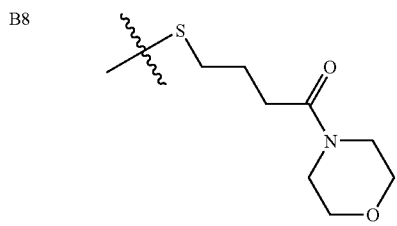 | C8 | 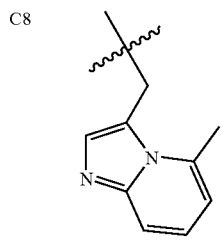 |
| | | B9 | 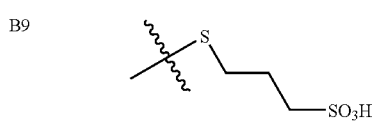 | | |
| | | B10 | 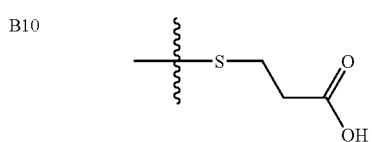 | | |
| | | B11 | 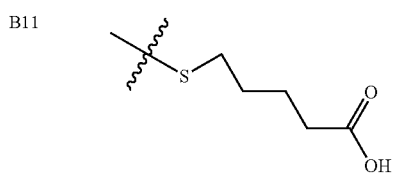 | | |
| | | B12 | 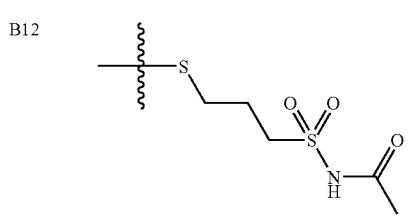 | | |
| | | B13 | 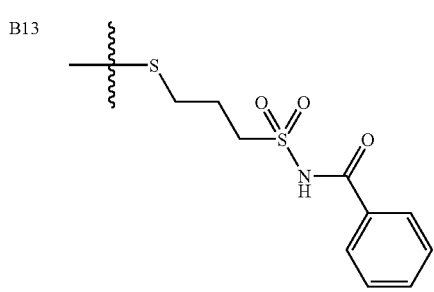 | | |
| | | B14 | 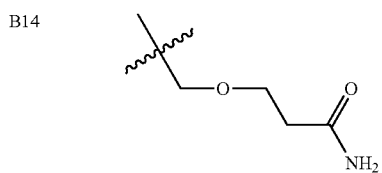 | | |
| | | B15 | 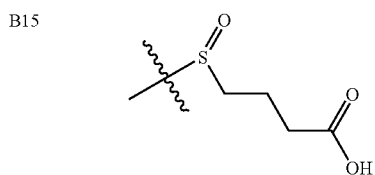 | | |

TABLE I-continued
B16 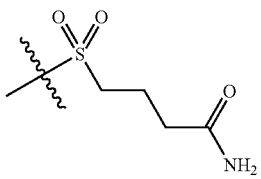
B17 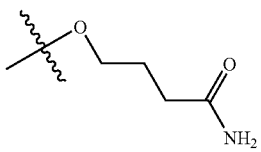
B18
B19
or the pharmaceutically acceptable salts thereof.
5. A compound of the formula (III):
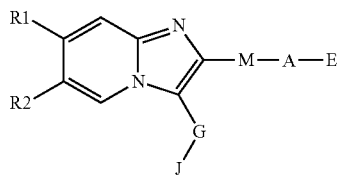   (III)
wherein for the Formula (III), the component
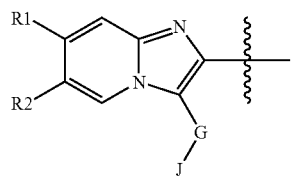
is chosen from A1-A15 in the table I below; in combination with any component
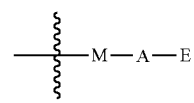
chosen from B1-B17 in the table II below;
TABLE II
| 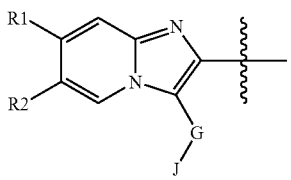 | 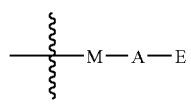 |
|---|---|
| A1 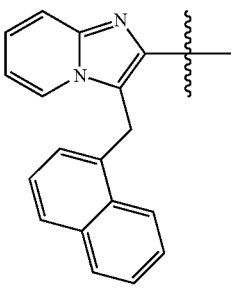 | B1 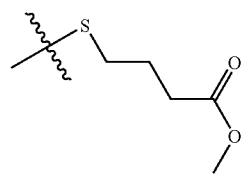 |

TABLE II-continued
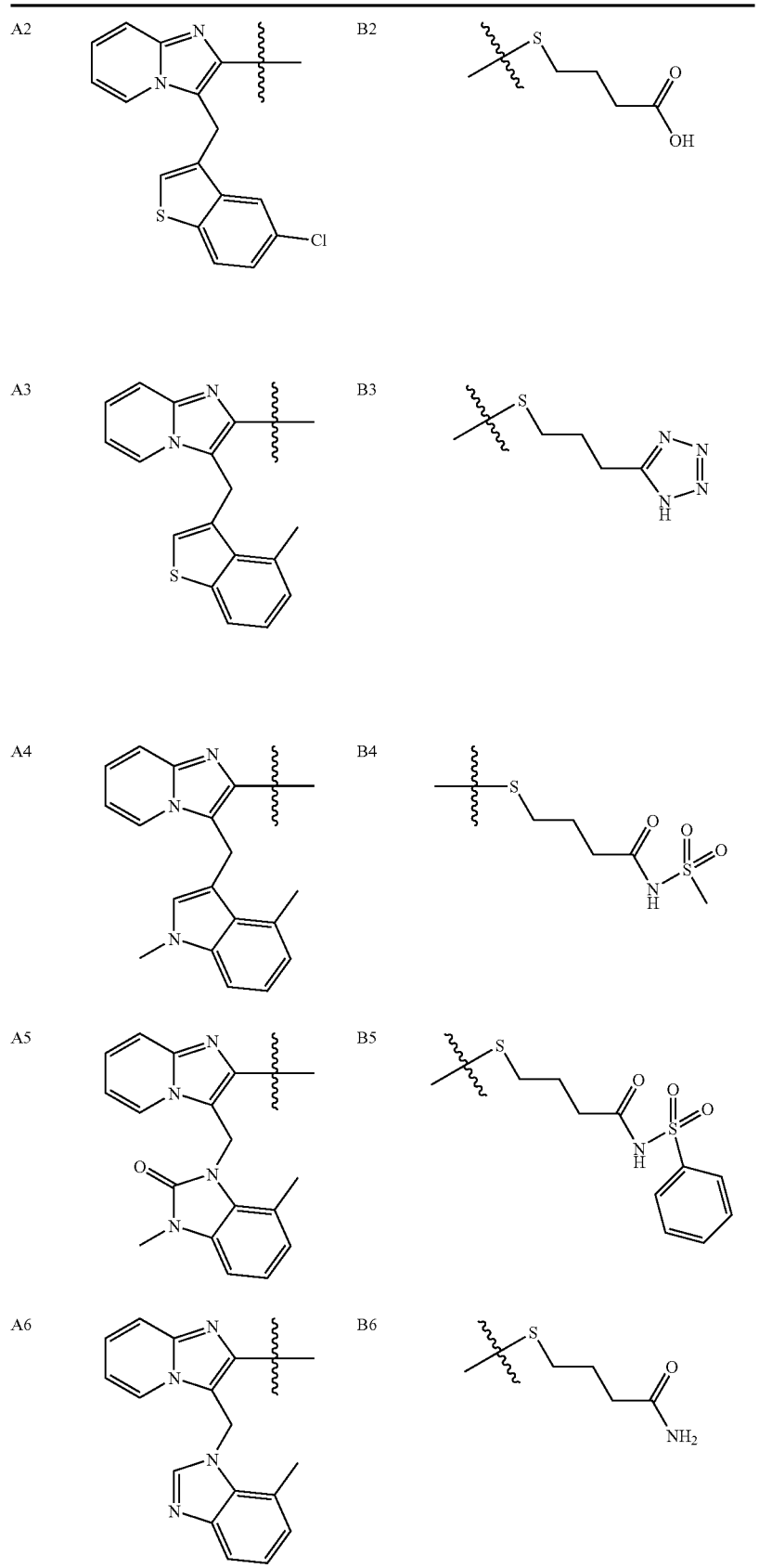

TABLE II-continued
| | | | |
|---|---|---|---|
| A7 | 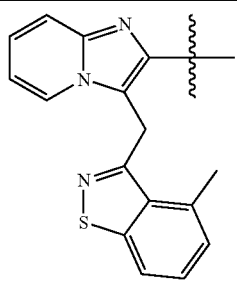 | B7 | 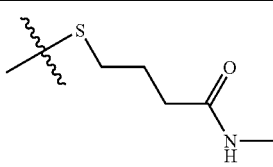 |
| A8 | 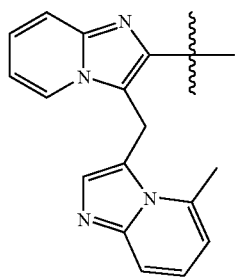 | B8 | 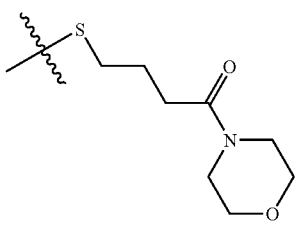 |
| A9 | 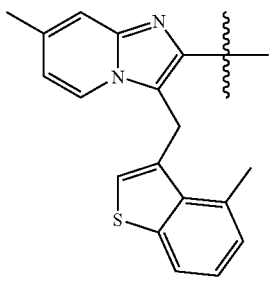 | B9 | 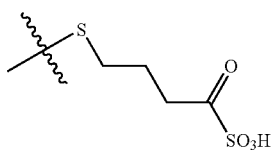 |
| A10 | 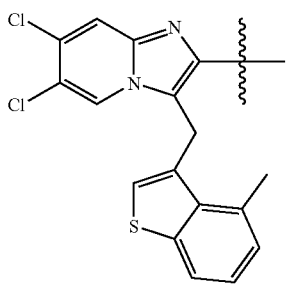 | B10 | 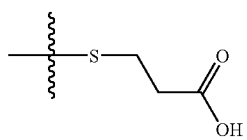 |
| A11 | 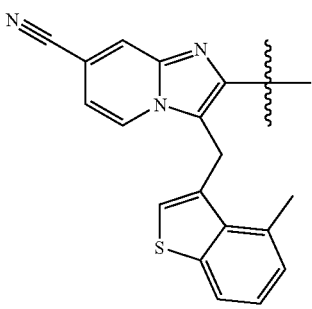 | B11 | 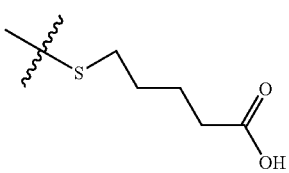 |

TABLE II-continued
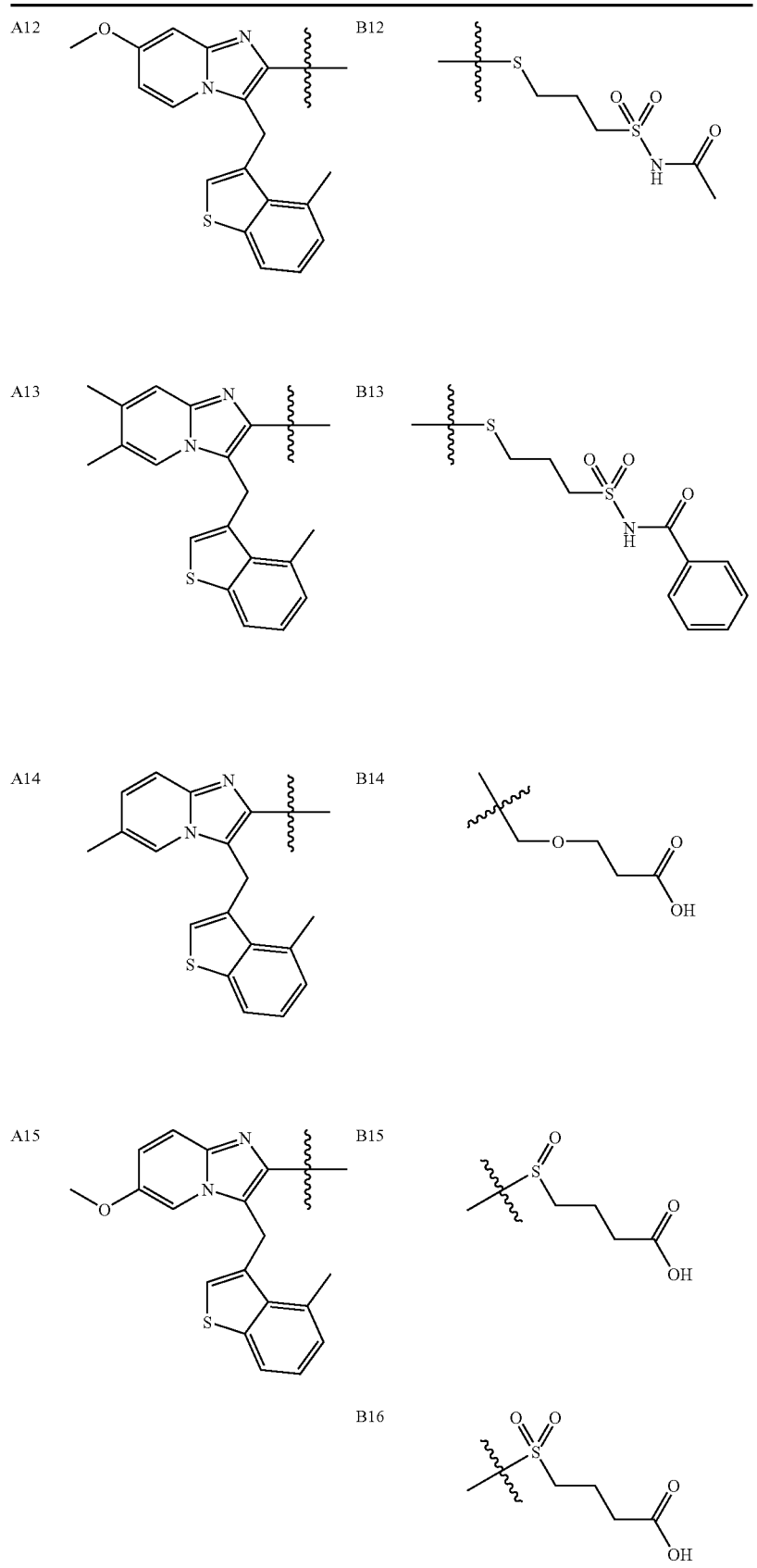

TABLE II-continued
| | |
|---|---|
| B17 | 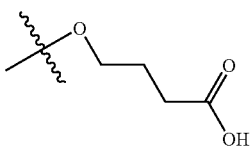 |
| B18 | |
| B19 | |
or the pharmaceutically acceptable salts thereof.
6. A compound chosen from
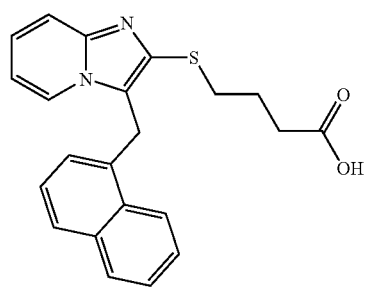
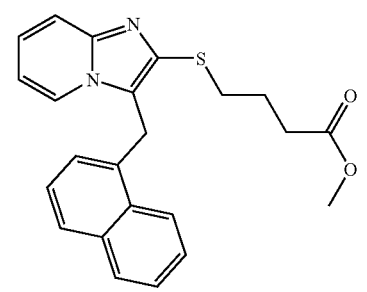
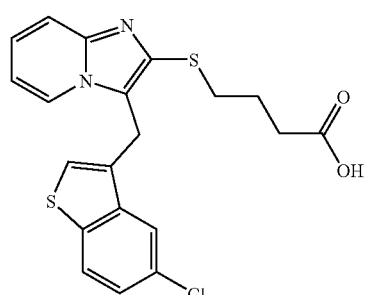
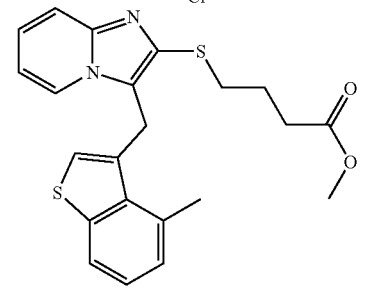
-continued
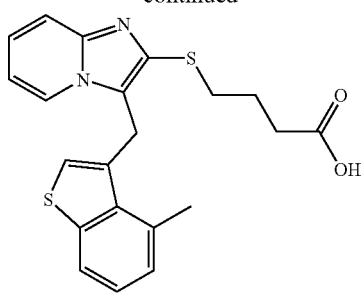
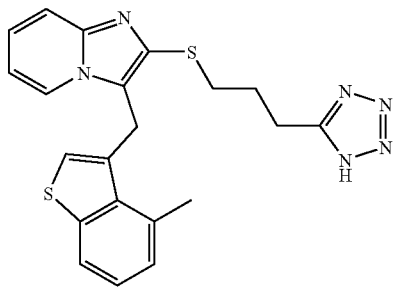
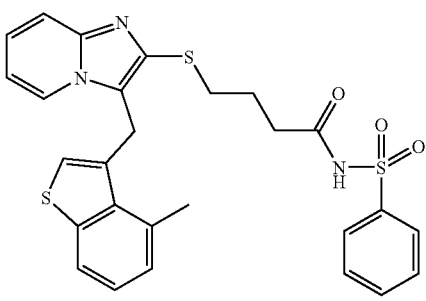
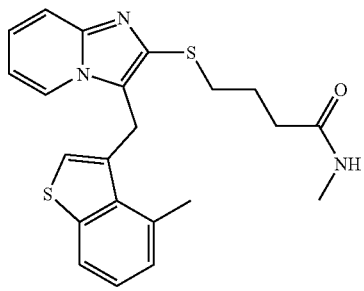

-continued
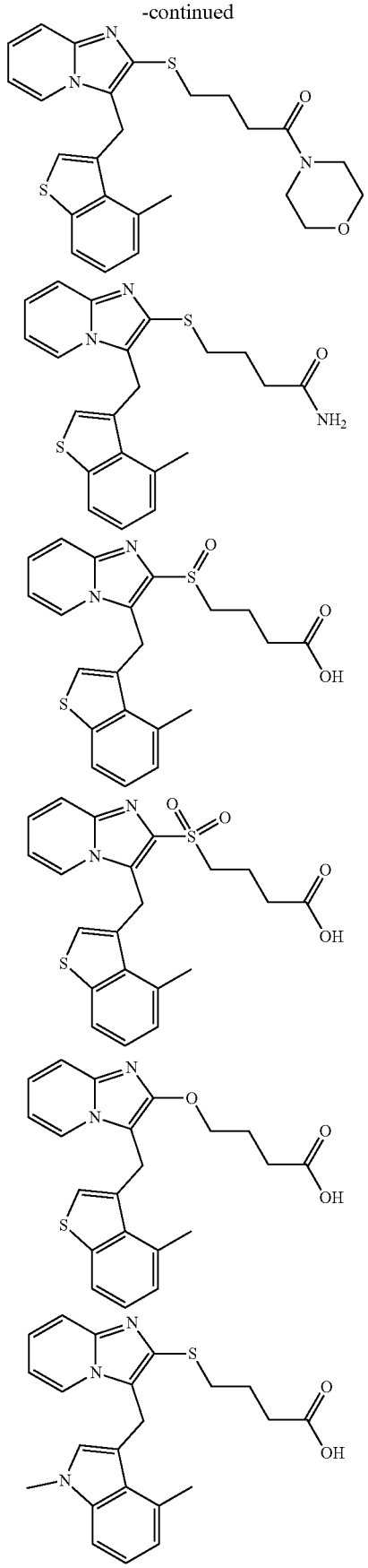
-continued
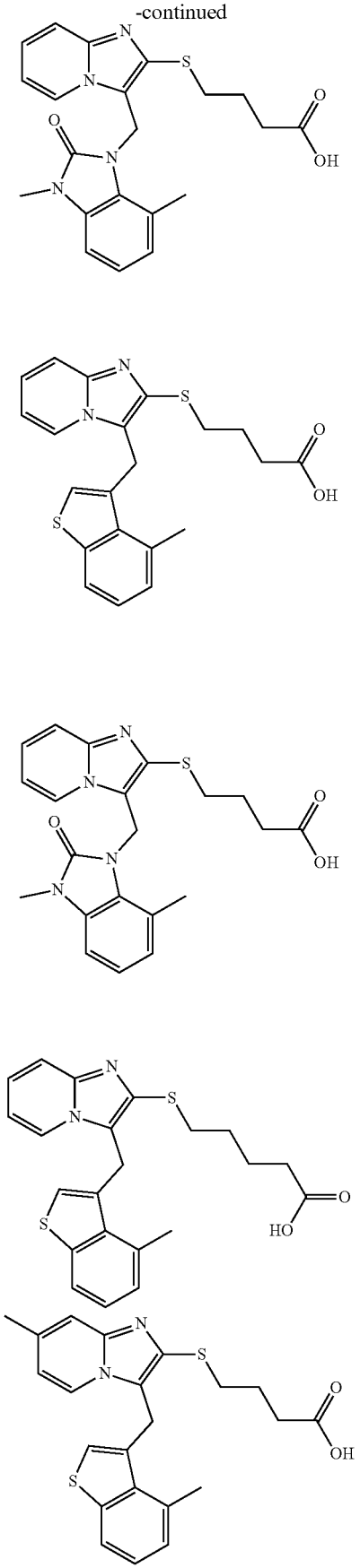

61
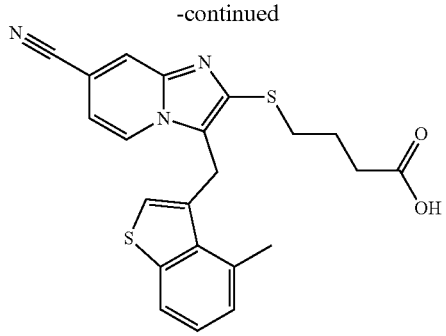
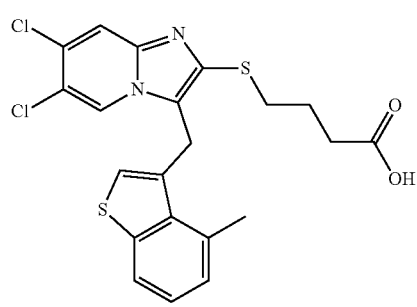
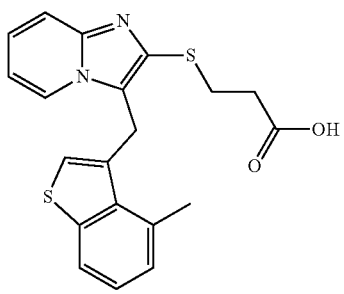
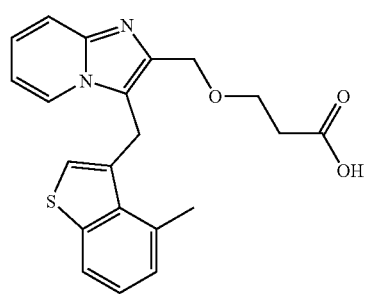
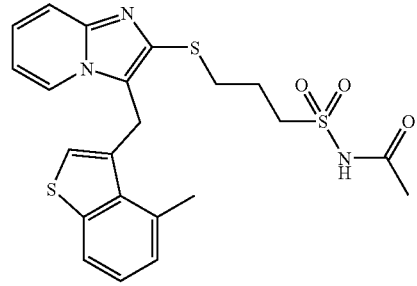
62
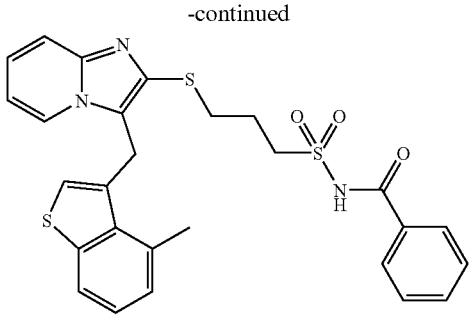
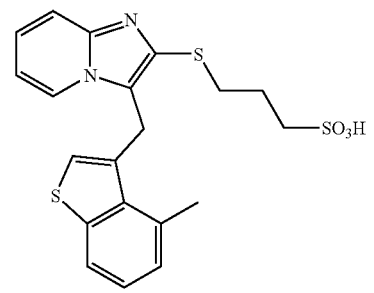
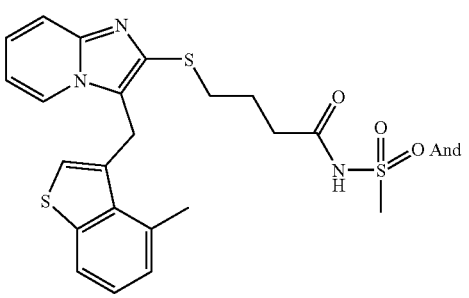
And
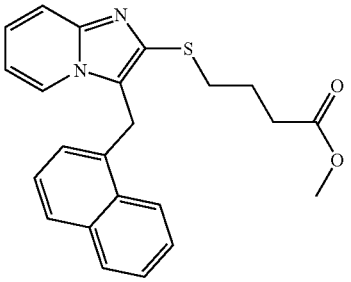
or the pharmaceutically acceptable salts thereof.
7. A compound chosen from
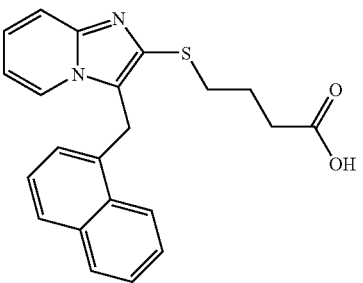

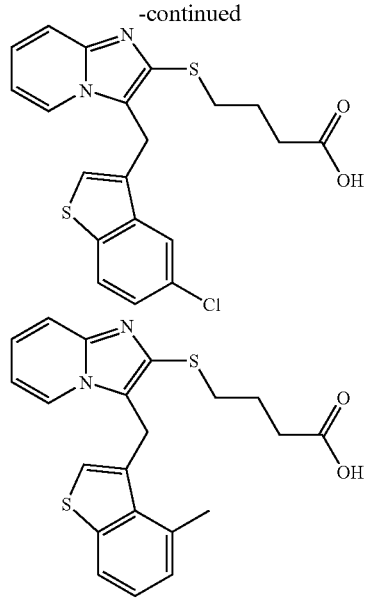
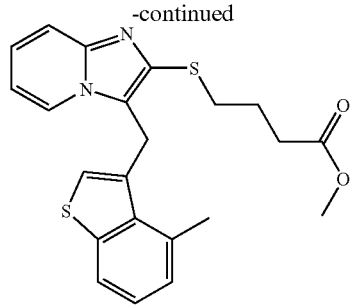
or the pharmaceutically acceptable salts thereof.
8. A pharmaceutical composition comprising a therapeutically effective amount of a compound according to claim 1.
* * * * *